United States Patent
Watanabe et al.

(10) Patent No.: US 8,304,096 B2
(45) Date of Patent: Nov. 6, 2012

(54) FUSED POLYCYCLIC AROMATIC COMPOUND AND ORGANIC LIGHT EMITTING DEVICE USING THE COMPOUND

(75) Inventors: Taiki Watanabe, Akishima (JP); Koichi Suzuki, Yokohama (JP); Kazunori Ueno, Glen Waverly (AU); Koichi Nakata, Mishima (JP); Takayuki Ito, Mobara (JP); Hiroki Ohrui, Kawasaki (JP); Akihiro Senoo, Kawasaki (JP); Naoki Yamada, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 169 days.

(21) Appl. No.: 13/002,119

(22) PCT Filed: Jul. 9, 2009

(86) PCT No.: PCT/JP2009/062844
§ 371 (c)(1),
(2), (4) Date: Dec. 30, 2010

(87) PCT Pub. No.: WO2010/008034
PCT Pub. Date: Jan. 21, 2010

(65) Prior Publication Data
US 2011/0095284 A1    Apr. 28, 2011

(30) Foreign Application Priority Data
Jul. 14, 2008 (JP) .................. 2008-182216

(51) Int. Cl.
*H01L 51/54* (2006.01)
(52) U.S. Cl. ........ 428/690; 428/917; 313/504; 313/505; 313/506; 257/40; 257/E51.05; 257/E51.026; 257/E51.032; 585/27
(58) Field of Classification Search .................. 428/690; 313/504, 505, 506; 257/40, E51.05, E51.026, 257/E51.032; 585/27
See application file for complete search history.

(56) References Cited

FOREIGN PATENT DOCUMENTS
| | | |
|---|---|---|
| JP | 10-189248 | 7/1998 |
| JP | 10-340783 | 12/1998 |
| JP | 11-012205 | 1/1999 |

*Primary Examiner* — Jennifer Chriss
*Assistant Examiner* — Gregory Clark
(74) *Attorney, Agent, or Firm* — Fitzpatrick, Cella, Harper & Scinto

(57) ABSTRACT

Provided are a novel fused polycyclic aromatic compound having a fluoranthene skeleton and an organic light emitting device having high efficiency and high durability. The organic light emitting device includes a fused polycyclic aromatic compound represented by the following general formula [1] or [2], and the organic light emitting device includes an anode, a cathode, an organic compound layer interposed between the anode and the cathode, in which at least one layer of the organic compound layers includes at least one kind of the fused polycyclic aromatic compound represented by the following general formula [1] or [2].

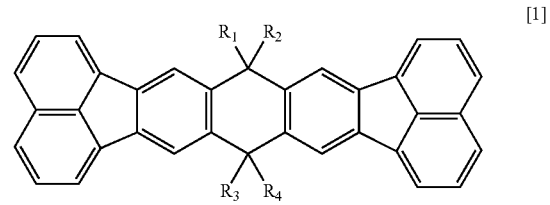

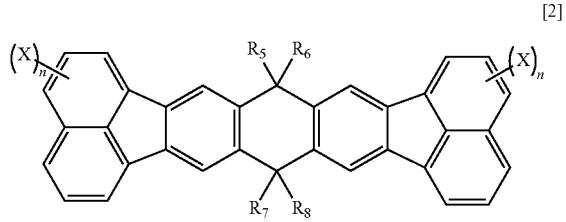

7 Claims, 3 Drawing Sheets

FUSED POLYCYCLIC AROMATIC COMPOUND AND ORGANIC LIGHT EMITTING DEVICE USING THE COMPOUND

TECHNICAL FIELD

The present invention relates to a fused polycyclic aromatic compound, and an organic light emitting device and a display apparatus using the compound.

BACKGROUND ART

An organic light emitting device is a device in which a thin film including a fluorescent organic compound or a phosphorescent organic compound is interposed between an anode and a cathode. Further, electrons and holes are injected from the respective electrodes and generate exciton, whereby the organic light emitting device emits light when the exciton returns to a ground state.

In recent years, there have been reported many technologies using a fluoranthene compound as a material for an organic light emitting device. For example, a fluoranthene compound having a substituent disclosed in Japanese Patent Application Laid-Open No. H10-189248 and a benzofluoranthene compound disclosed in Japanese Patent Application Laid-Open No. H11-012205 are exemplified. Here, Japanese Patent Application Laid-Open Nos. H10-189248 and 11-012205 indicate that the light emitting devices using fluoranthene compounds have good emission efficiency, and thus, usefulness of a compound containing a fluoranthene skeleton in its molecules is being recognized. However, in the case of considering the compound having a fluoranthene skeleton as an organic material for constituting a display of a personal computer or a television, there has not yet been found a compound having a fluoranthene skeleton at a level of having both efficiency and stability and having resistance to practical use. Therefore, a compound having a fluoranthene skeleton and contributing to higher luminance and longer lifetime of an organic light emitting device has been demanded.

DISCLOSURE OF THE INVENTION

An object of the present invention is to provide a novel fused polycyclic aromatic compound having a fluoranthene skeleton. In addition, another object of the present invention is to provide an organic light emitting device having high efficiency and high durability.

The inventors of the present invention have earnestly studied so as to solve the above problem, thereby achieving the present invention. That is, a fused polycyclic aromatic compound of the present invention is a compound represented by the following general formula [I] or [II]:

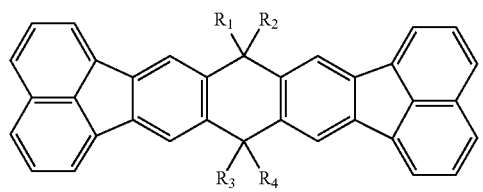

[1]

where $R_1$ to $R_4$ each represent hydrogen, a halogen atom, a substituted or unsubstituted alkyl group, a substituted or unsubstituted aralkyl group, or a substituted or unsubstituted aryl group,

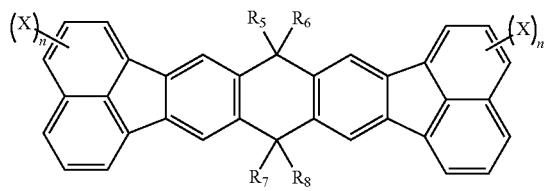

[2]

where: $R_5$ to $R_8$ each represent hydrogen, a halogen atom, a substituted or unsubstituted alkyl group, a substituted or unsubstituted aralkyl group, or a substituted or unsubstituted aryl group; X represents a substituted or unsubstituted alkyl group, a substituted or unsubstituted aralkyl group, a substituted or unsubstituted aryl group, a substituted or unsubstituted heterocyclic group, a substituted amino group, a substituted boryl group, a substituted silyl group, a cyano group, or a halogen atom; and n represents an integer of 0 to 6, and when n represents 2 or more, a plurality of X's may be the same as or different from each other and the plurality of X's may bond to each other to form a ring structure.

According to the present invention, a novel fused polycyclic aromatic compound having a fluoranthene skeleton can be provided. In addition, according to the present invention, an organic light emitting device having high efficiency and high durability can be provided. Further, according to the present invention, an organic light emitting device capable of being produced easily by a relatively inexpensive coating method can be provided.

Further features of the present invention will become apparent from the following description of exemplary embodiments with reference to the attached drawings.

BRIEF DESCRIPTION OF THE DRAWINGS

FIG. 1A is a cross-sectional view illustrating a first embodiment, FIG. 1B is a cross-sectional view illustrating a second embodiment, and FIG. 1C is a cross-sectional view illustrating a third embodiment.

BEST MODE FOR CARRYING OUT THE INVENTION

Figure 1A:
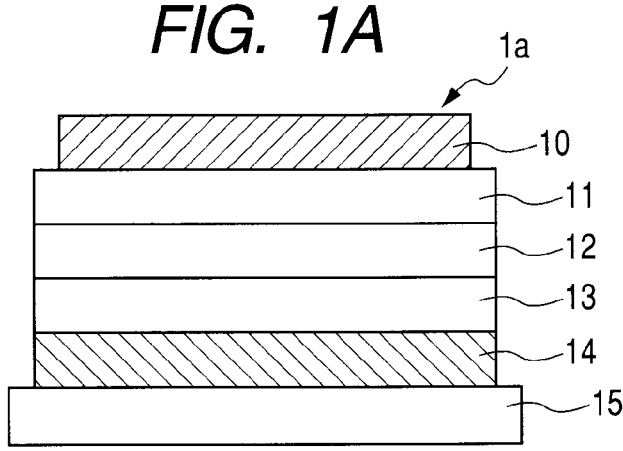
FIGS. 1A, 1B, and 1C are cross-sectional views illustrating examples of embodiments of an organic light emitting device of the present invention.

Hereinafter, the present invention will now be described in detail in accordance with the accompanying drawings.

First, a fused polycyclic aromatic compound of the present invention is described.

The fused polycyclic aromatic compound of the present invention is a compound represented by the following general formula [1] or [2].

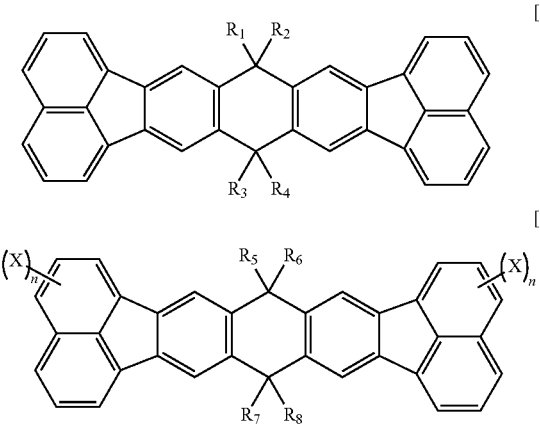

First, the compound represented by the formula [1] is described.

In the formula [1], $R_1$ to $R_4$ each represent hydrogen, a halogen atom, a substituted or unsubstituted alkyl group, a substituted or unsubstituted aralkyl group, or a substituted or unsubstituted aryl group.

Examples of the halogen atom represented by $R_1$ to $R_4$ include fluorine, chlorine, bromine, and iodine.

Examples of the alkyl group represented by $R_1$ to $R_4$ include a methyl group, an ethyl group, a propyl group, an isopropyl group, a butyl group, an isobutyl group, a secondary butyl group, a tertiary butyl group, a pentyl group, a hexyl group, a cyclopropyl group, a cyclopentyl group, a cyclohexyl group, and a fluorinated alkyl group (such as a trifluoromethyl group or a pentafluoroethyl group).

Examples of the aralkyl group represented by $R_1$ to $R_4$ include a benzyl group, a phenethyl group, a naphthyl methyl group, and a naphthyl ethyl group.

Examples of the aryl group represented by $R^1$ to $R^4$ include a phenyl group, a naphthyl group, a pentalenyl group, an indenyl group, an azulenyl group, an anthryl group, a pyrenyl group, an indacenyl group, an acenaphthenyl group, a phenanthryl group, a phenarenyl group, a fluoranthenyl group, an acephenanthryl group, an aceanthryl group, a triphenylenyl group, a chrysenyl group, a naphthacenyl group, a perylenyl group, a pantacenyl group, a biphenyl group, a terphenyl group, and a fluorenyl group.

Examples of the substituents that the alkyl group, aralkyl group, and aryl group may further have include: alkyl groups such as a methyl group, an ethyl group, an n-propyl group, a fluorinated alkyl group (such as a trifluoromethyl group or a pentafluoroethyl group); aralkyl groups such as a benzyl group and a phenethyl group; aryl groups such as a phenyl group, a biphenyl group, and a terphenyl group; heterocyclic groups such as a thienyl group, a pyrrolyl group, a pyridyl group, a bipyridyl group, an oxazolyl group, an oxadiazolyl group, a thiazolyl group, and a thiadiazolyl group; fused polycyclic aromatic groups such as a naphthyl group and a phenanthryl group; fused polycyclic heterocyclic groups such as a quinolyl group, a carbazolyl group, an acridinyl group, and a phenanthrolyl group; aryloxy groups such as a phenoxyl group and a naphthoxyl group; substituted amino groups such as a dimethylamino group, a diethylamino group, a diphenylamino group, a ditolylamino group, a dianisolylamino group, a 9,9-dimethyl-9H-fluorenyl phenylamino group, a difluorenyl group, a naphthylphenylamino group, and a dinaphthylamino group; substituted boryl groups such as a diphenylboryl group and a dimesitylboryl group; substituted silyl groups such as a trimethylsilyl group and a triphenylsilyl group; substituted germyl groups such as trimethyl germyl group and a triphenyl germyl group; halogen atoms such as fluorine, chlorine, bromine, and iodine; and deuterium.

Next, the compound represented by the formula [2] is described.

In the formula [2], $R_5$ to $R_8$ each represent hydrogen, a halogen atom, a substituted or unsubstituted alkyl group, a substituted or unsubstituted aralkyl group, or a substituted or unsubstituted aryl group. Note that specific examples of the halogen atom, alkyl group, aralkyl group, and aryl group represented by $R_5$ to $R_8$, and the substituents which the alkyl group, aralkyl group, and aryl group may have are the same as those for $R_1$ to $R_4$ in the formula [1].

In the formula [2], X represents a substituted or unsubstituted alkyl group, a substituted or unsubstituted aralkyl group, a substituted or unsubstituted aryl group, a substituted or unsubstituted heterocyclic group, a substituted amino group, a substituted boryl group, a substituted silyl group, a cyano group, a halogen atom, a styryl group, or deuterium.

Examples of the alkyl group represented by X include a methyl group, an ethyl group, a propyl group, an isopropyl group, a butyl group, an isobutyl group, a secondary butyl group, a tertiary butyl group, a pentyl group, a hexyl group, a cyclopropyl group, a cyclopentyl group, a cyclohexyl group, and a fluorinated alkyl group (such as trifluoromethyl group or a pentafluoroethyl group).

Examples of the aralkyl group represented by X include a benzyl group, a phenethyl group, a naphthylmethyl group, and a naphthylethyl group.

Examples of the aryl group represented by X include a phenyl group, a naphthyl group, a pentalenyl group, an indenyl group, an azulenyl group, an anthryl group, a pyrenyl group, a indacenyl group, an acenaphthenyl group, a phenanthryl group, a phenarenyl group, a fluoranthenyl group, an acephenanthryl group, an aceanthryl group, a triphenylenyl group, a chrysenyl group, a naphthacenyl group, a perylenyl group, a pentacenyl group, a biphenyl group, a terphenyl group, and a fluorenyl group.

Examples of the heterocyclic group represented by X include a thienyl group, a pyrrolyl group, a pyridyl group, an oxazolyl group, an oxadiazolyl group, a thiazolyl group, a thiadiazolyl group, a terthienyl group, a carbazolyl group, an acridinyl group, a phenanthrolyl group, and a benzodiazolyl group.

Examples of the substituted amino group represented by X include a dimethyl amino group, a diethyl amino group, dibenzyl amino group, a diphenyl amino group, a ditolyl amino group, a dianisolyl amino group, and a 9,9-dimethyl-9H-fluorenylphenyl amino group.

Examples of the substituted boryl group represented by X include a diphenyl boryl group, a ditolyl boryl group, a dimesityl boryl group, and a dinapthyl boryl group.

Examples of the substituted silyl group represented by X include a trimethylsilyl group, a triethylsilyl group, and a triphenylsilyl group.

Examples of the halogen atom represented by X include fluorine, chlorine, bromine, and iodine.

Examples of the substituents that the above alkyl group, aralkyl group, aryl group, and heterocyclic group may have include: alkyl groups such as a methyl group, an ethyl group, and an n-propyl group; fluorinated alkyl groups such as a trifluoromethyl group and a pentafluoroethyl group; aralkyl groups such as a benzyl group and a phenethyl group; aryl groups such as a phenyl group, a biphenyl group, and a terphenyl group; heterocyclic groups such as a thienyl group, a pyrrolyl group, a pyridyl group, a bipyridyl group, an oxazolyl group, an oxadiazolyl group, a thiazolyl group, and a thiadiazolyl group; fused polycyclic aromatic groups such as a naphthyl group and a phenanthryl group; fused polycyclic heterocyclic groups such as a quinolyl group, a carbazolyl group, an acridinyl group, and a phenanthrolyl group; aryloxy groups such as a phenoxyl group and a naphthoxyl group; substituted amino groups such as a dimethylamino group, a diethylamino group, a diphenylamino group, a ditolylamino group, a dianisolylamino group, a 9,9-dimethyl-9H-fluorenylphenylamino group, a difluorenyl group, a naphthylphenylamino group, and a dinaphthylamino group; substituted boryl groups such as a diphenylboryl group and a dimesitylboryl group; substituted silyl groups such as a trimethylsilyl group and a triphenylsilyl group; substituted germyl groups such as a trimethyl germyl group and a triphenyl germyl group; halogen atoms such as fluorine, chlorine, bromine, and iodine; and deuterium.

In the formula [2], n represents an integer of 0 to 6.

In addition, when n represents 2 or more, a plurality of X's may be the same as or different from each other. Further, when n represents 2 or more, the plurality of X's may bond to each other to form ring structures represented below. The ring structures may further have substituents such as a tertiary butyl group, a phenyl group, and a tolyl group.

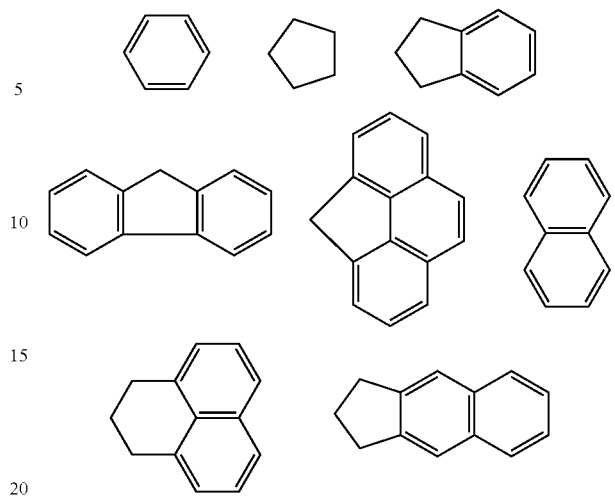

Hereinafter, specific examples of the fused polycyclic aromatic compound of the present invention are described, but the present invention is not of course limited thereto.

(1)

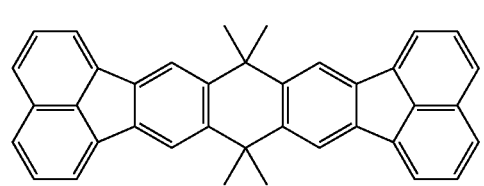

(2)

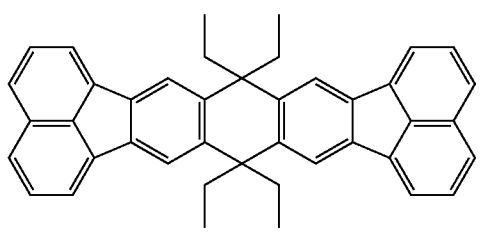

(3)

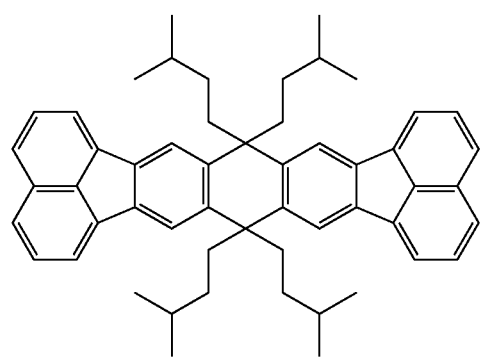

(4)

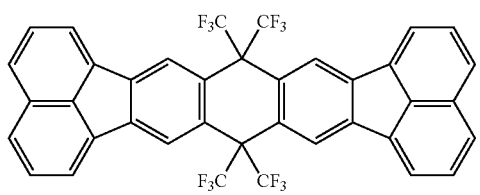

(5)

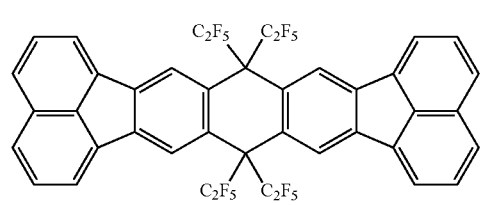

(6)

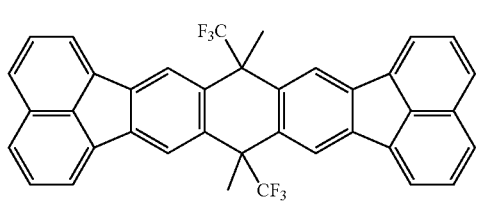

(7)
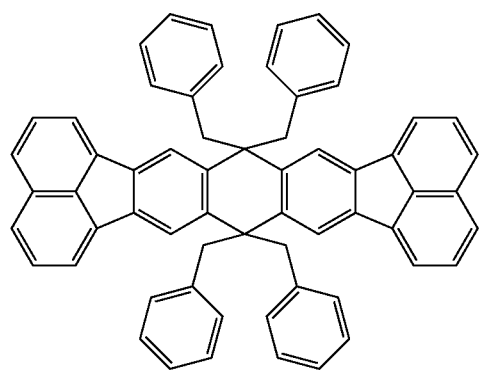
(8)
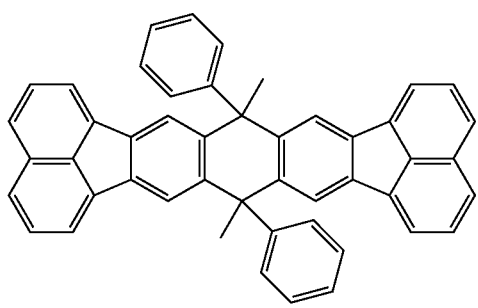
(9)
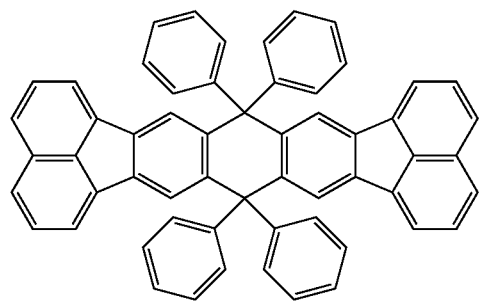
(10)
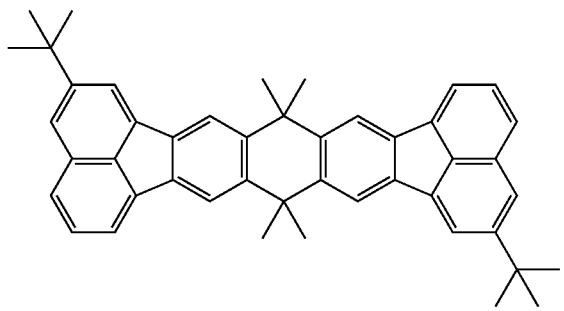
(11)
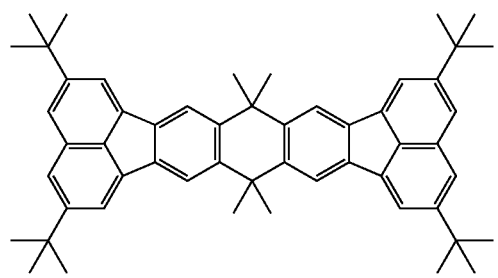
(12)
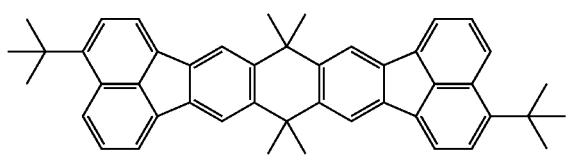
(13)
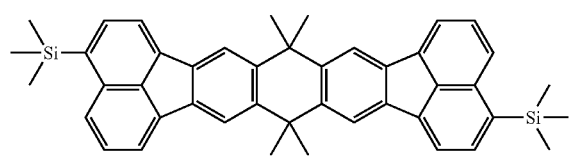
(14)
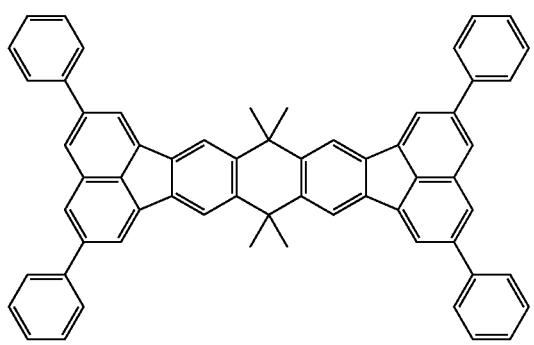

-continued
(15)
(16)
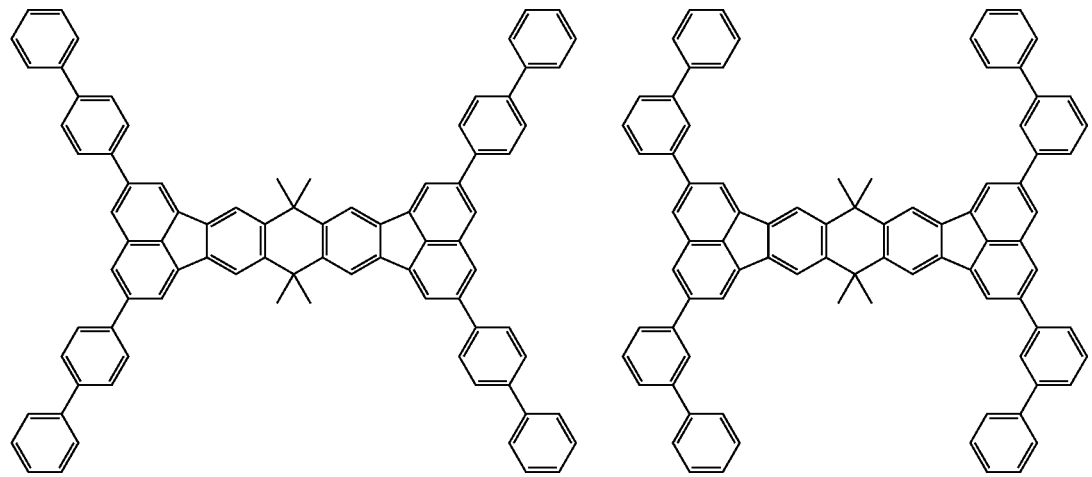
(17)
(18)
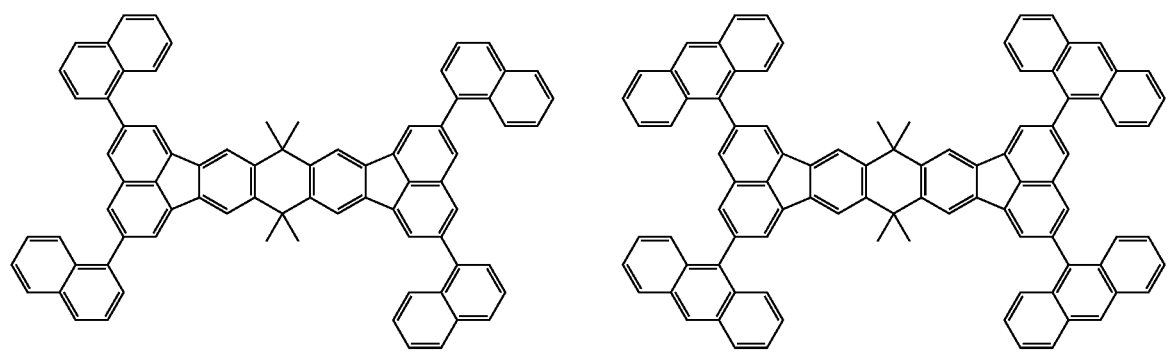
(19)
(20)
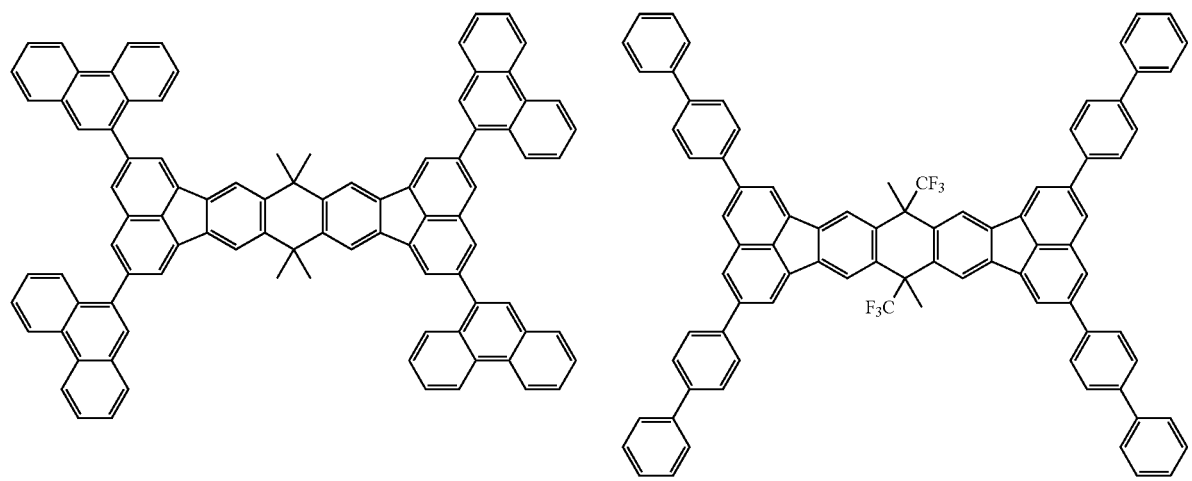

-continued
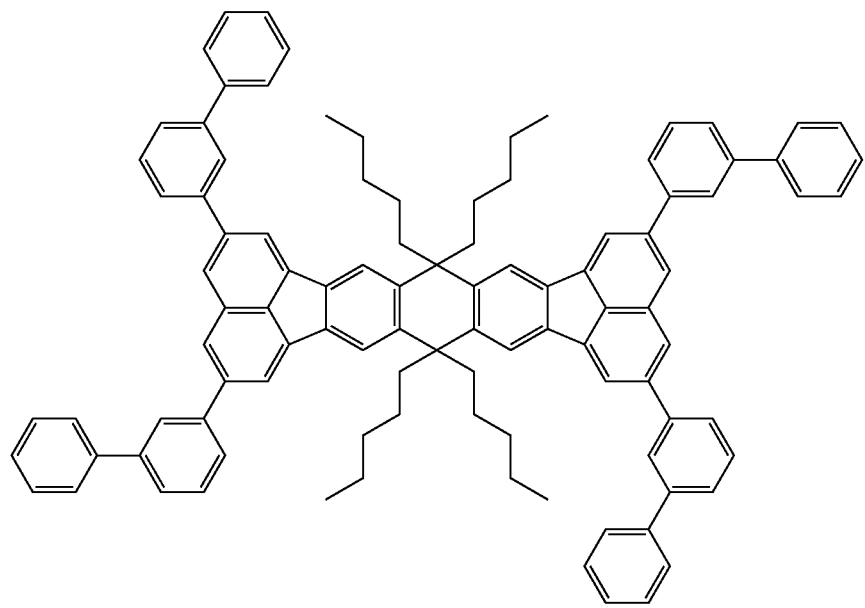
(21)
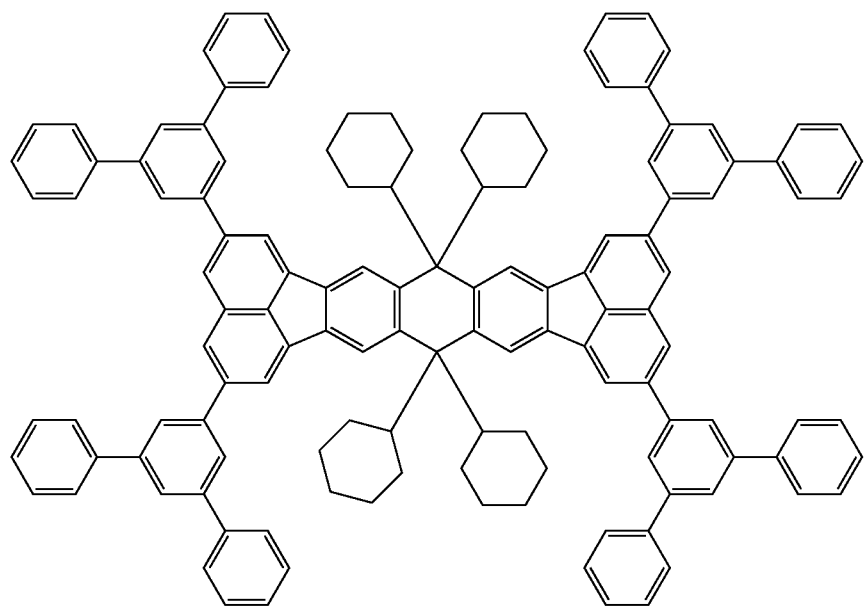
(22)
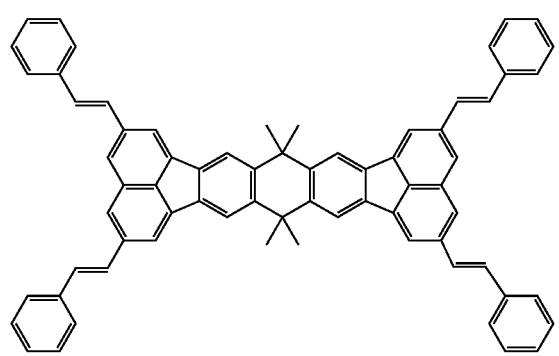
(23)
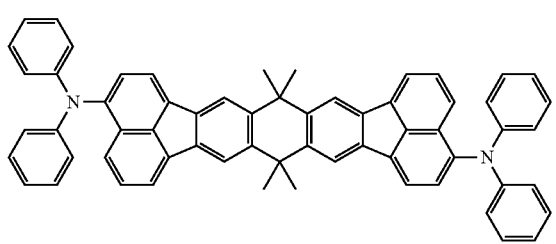
(24)

-continued
(25)
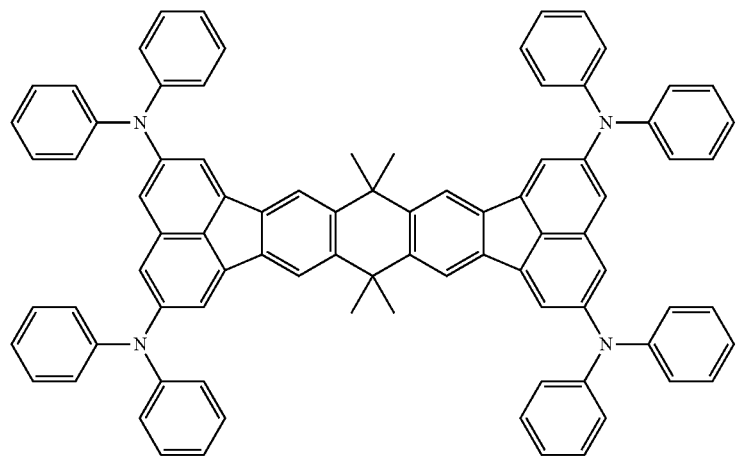
(26)
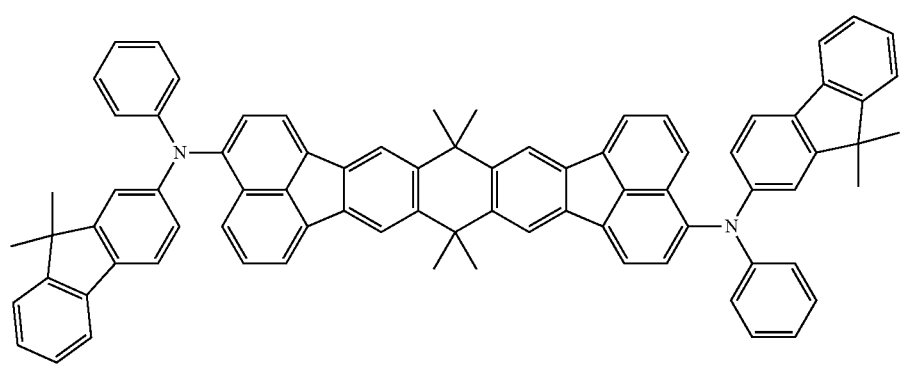
(27)
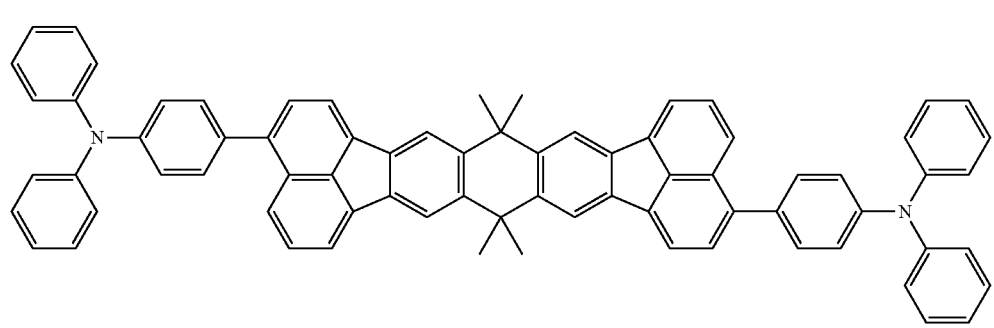
(28)
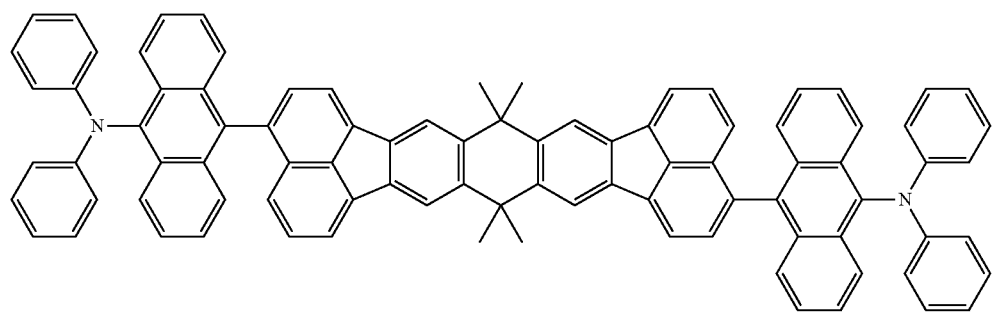

(29)
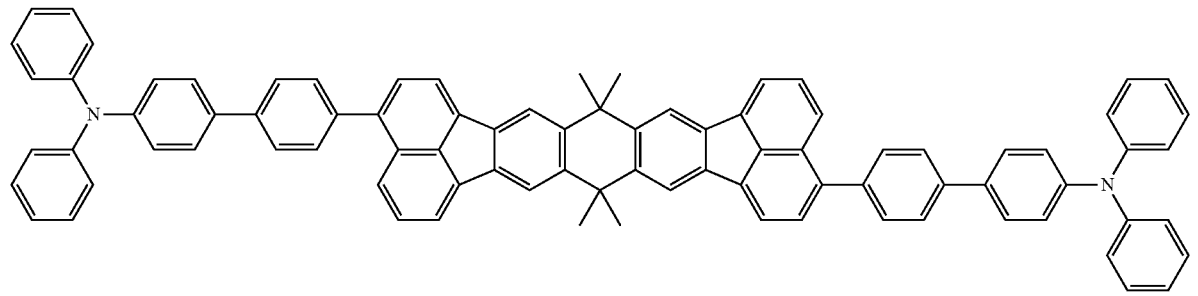
(30)
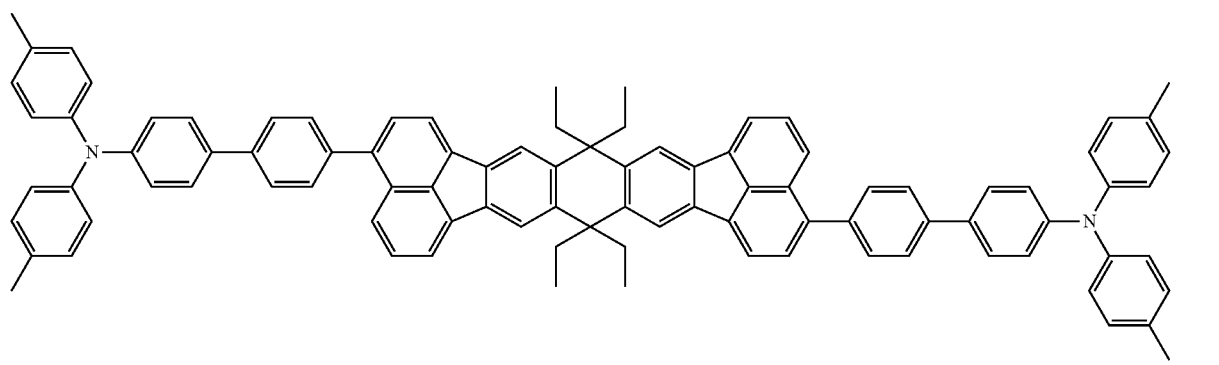
(31) (32)
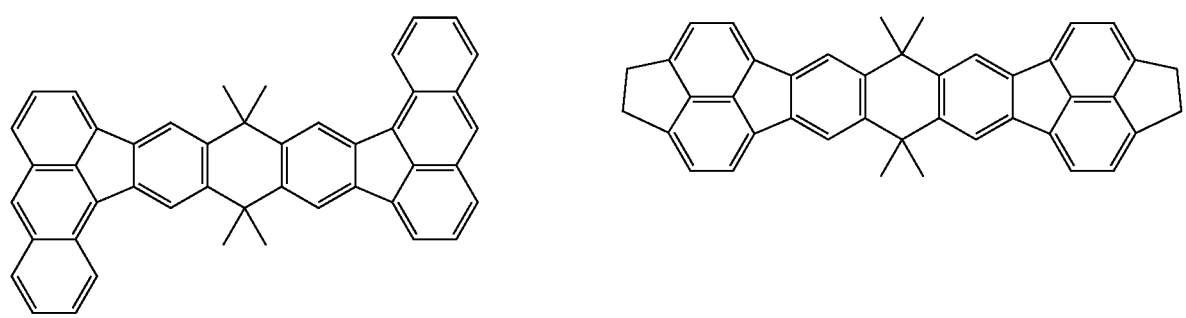
(33) (34)
(35) (36)
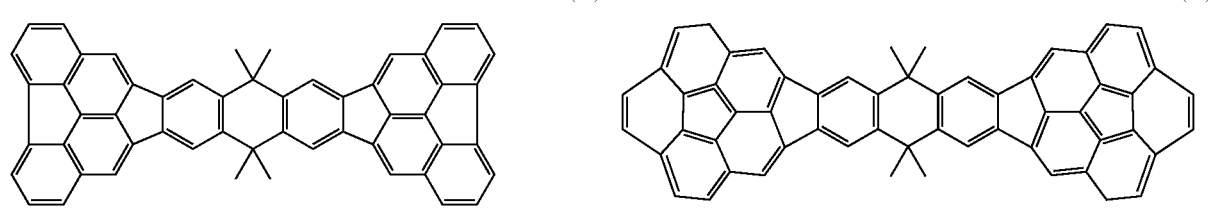

-continued
(37)
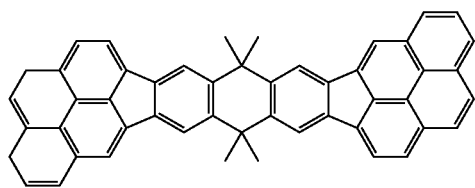
(38)
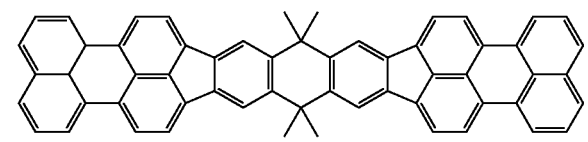
(39)
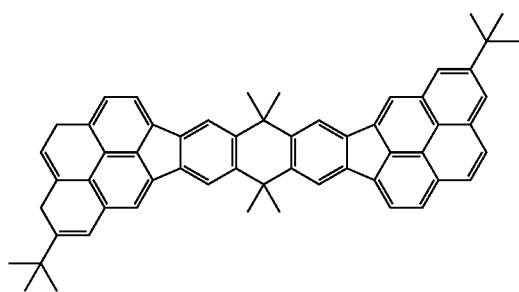
(40)
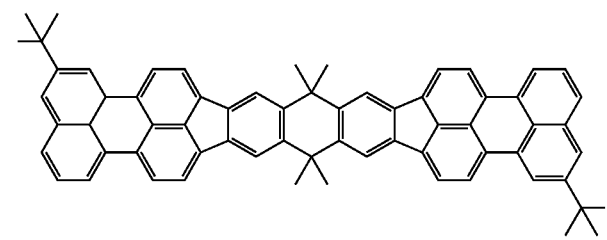
(41)
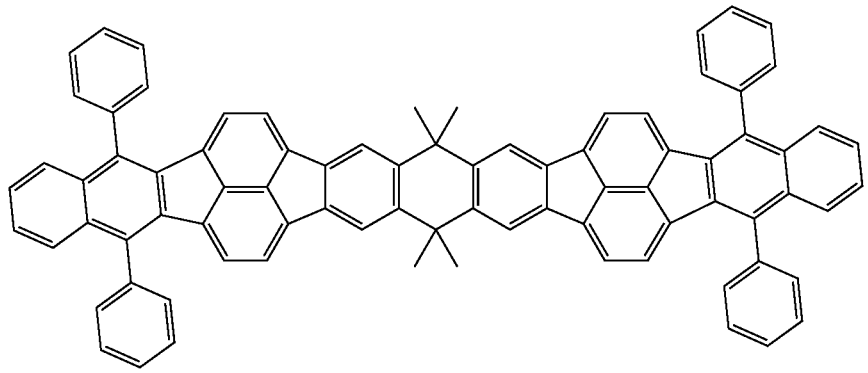
(42)
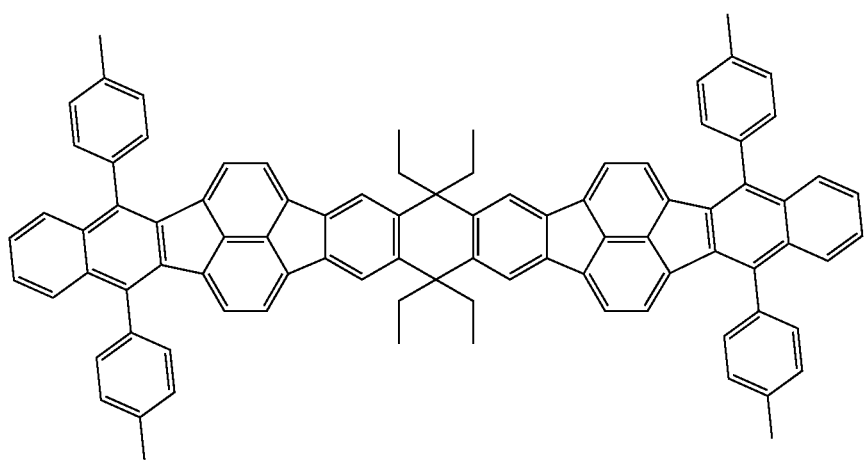

-continued
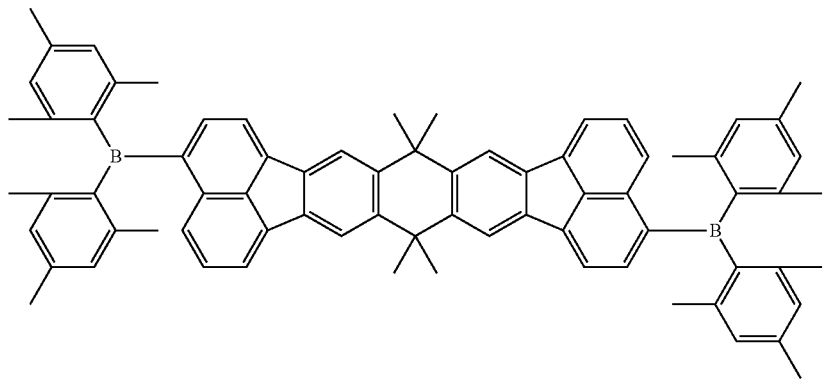
(43)
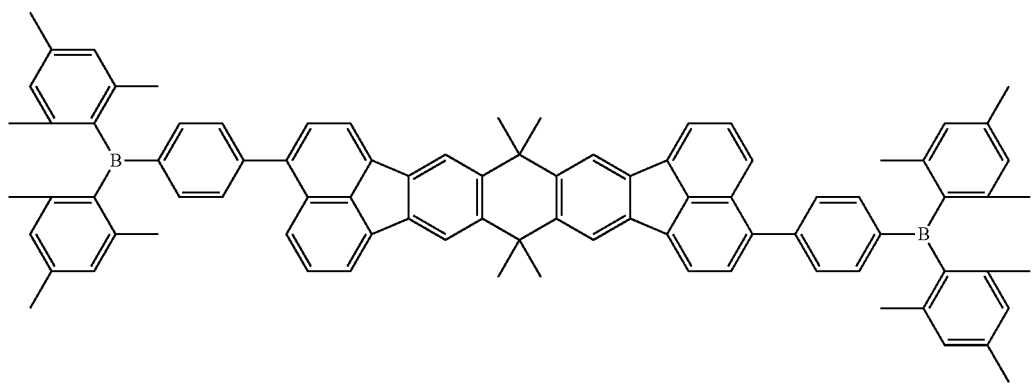
(44)
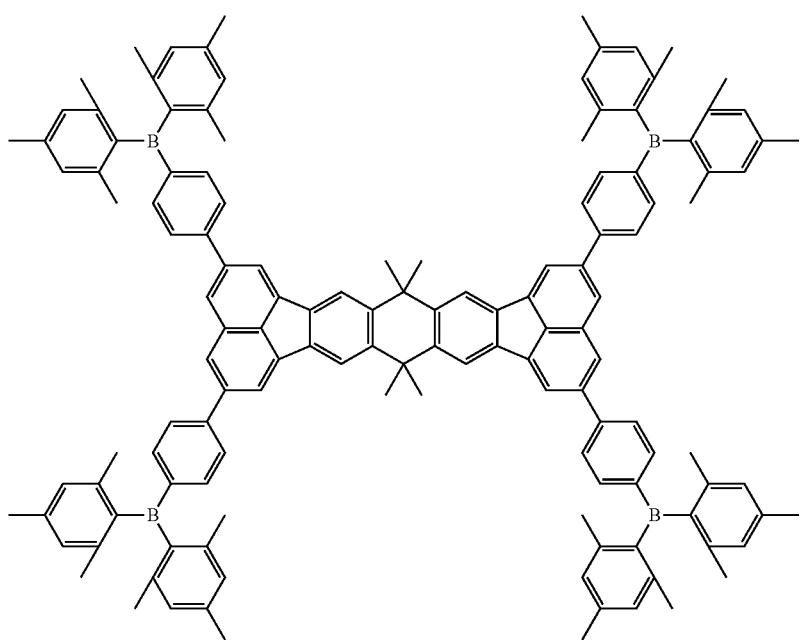
(45)

(46)
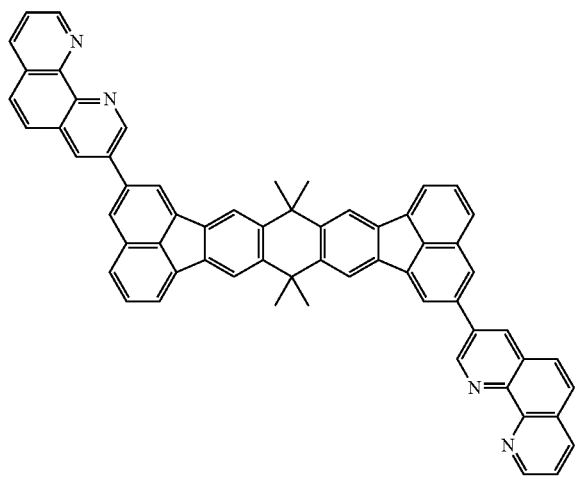
(47)
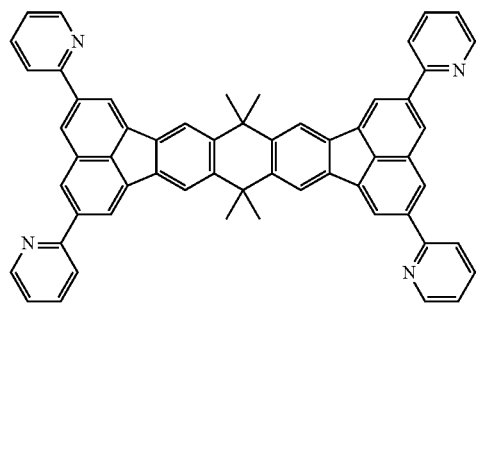
(48)
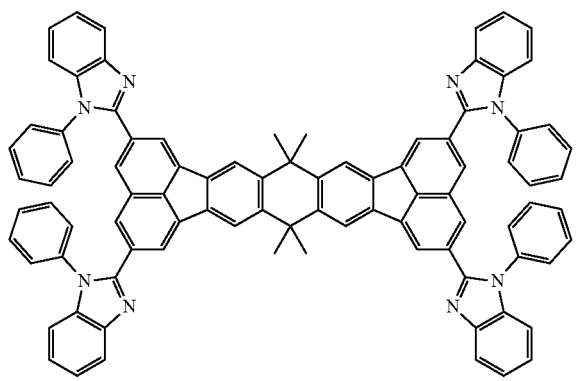
(49)
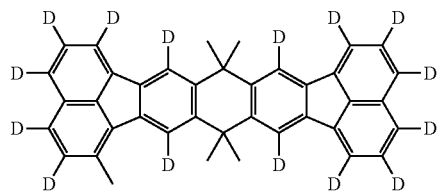
By the way, the fused polycyclic aromatic compound represented by the formula [2] is preferably synthesized by using, as a raw material, a boron compound represented by the following general formula [3] or the general formula [4].
[3]
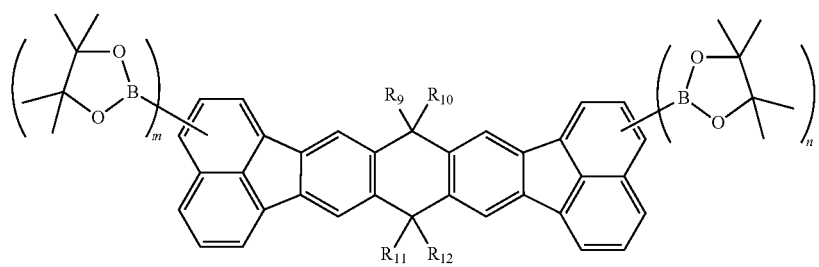
[4]
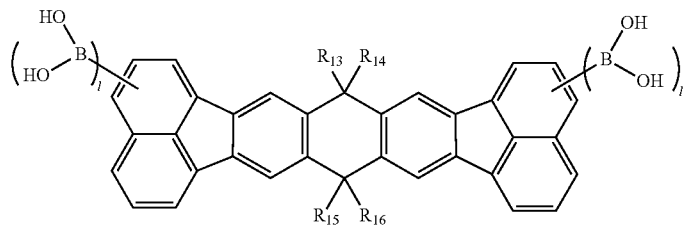

In the formula [3], $R_9$ to $R_{12}$ each represent hydrogen, a halogen atom, a substituted or unsubstituted alkyl group, a substituted or unsubstituted aralkyl group, or a substituted or unsubstituted aryl group. Note that specific examples of the halogen atom, alkyl group, aralkyl group, and aryl group represented by $R_9$ to $R_{12}$ and the substituent which the alkyl group, aralkyl group, and aryl group may further have are the same as those for $R_5$ to $R_8$ in the formula [2] (i.e., $R_1$ to $R_4$ in the formula [1]).

In the formula [3], m represents an integer of 1 to 6.

In the formula [4], $R_{13}$ to $R_{16}$ each represent hydrogen, a halogen atom, a substituted or unsubstituted alkyl group, a substituted or unsubstituted aralkyl group, or a substituted or unsubstituted aryl group. Note that specific examples of the halogen atom, alkyl group, aralkyl group, and aryl group represented by $R_{13}$ to $R_{16}$ and the substituent which the alkyl group, aralkyl group, and aryl group may further have are the same as those for $R_5$ to $R_8$ in the formula [2] (i.e., $R_1$ to $R_4$ in the formula [1]).

In the formula [4], l represents an integer of 1 to 6.

Hereinafter, specific examples of the boron compound are described, but the present invention is not of course limited thereto.

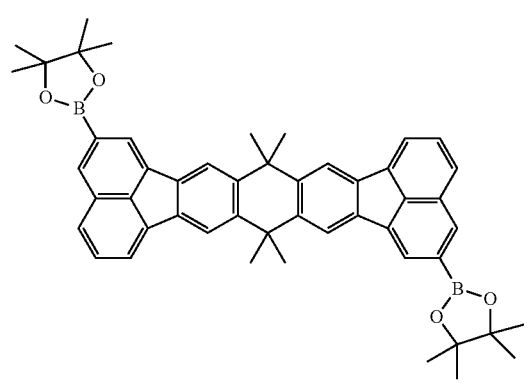

(50)

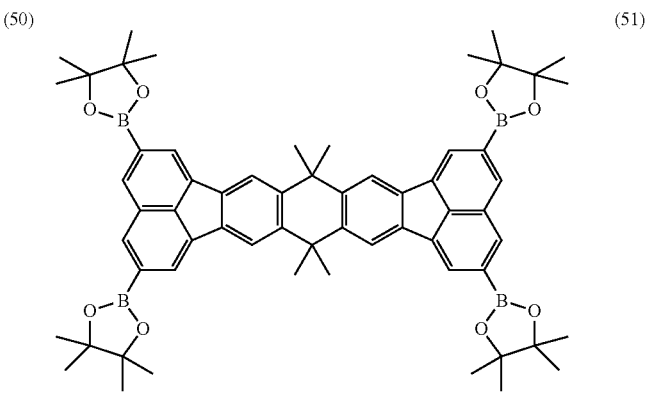

(51)

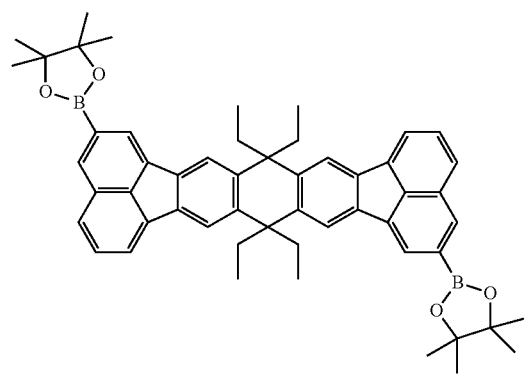

(52)

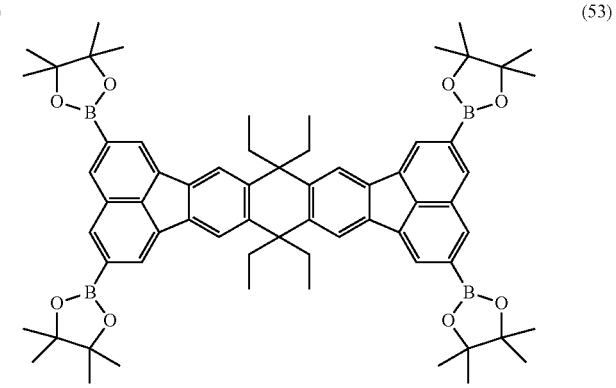

(53)

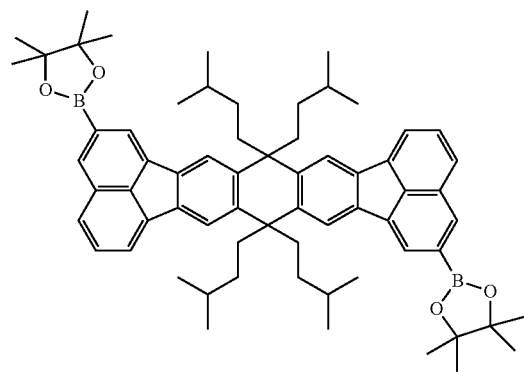

(54)

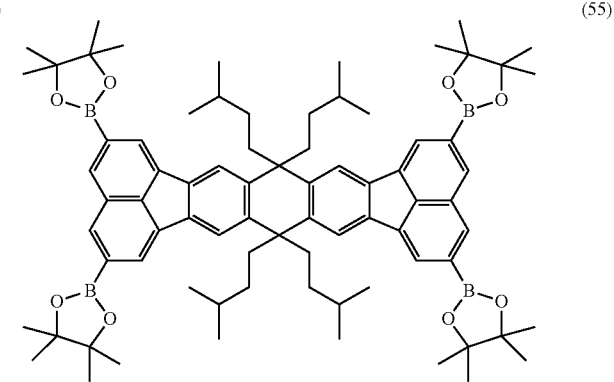

(55)

-continued
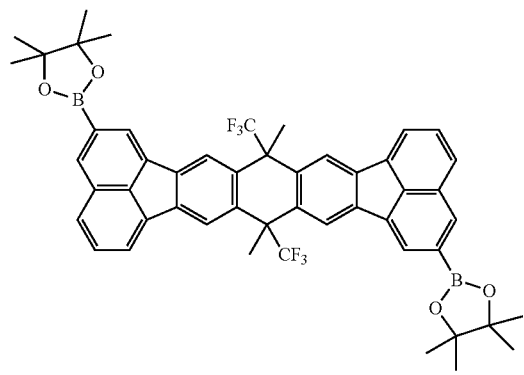
(56)
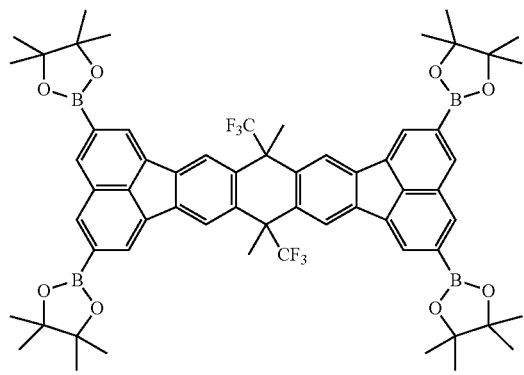
(57)
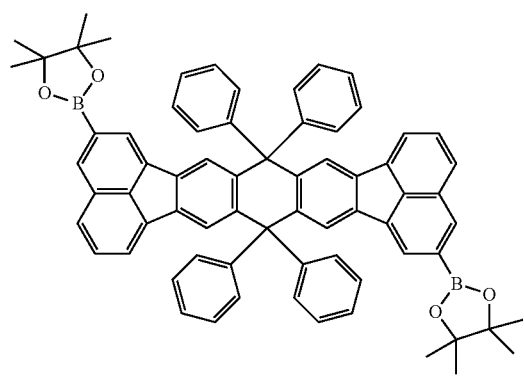
(58)
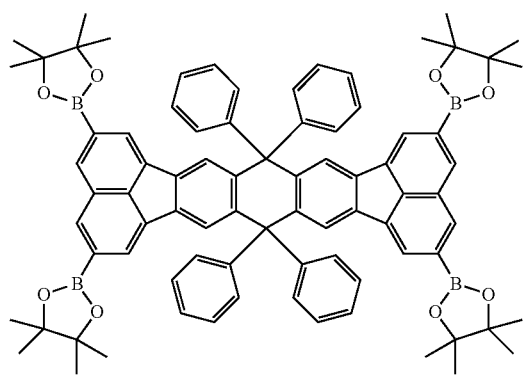
(59)
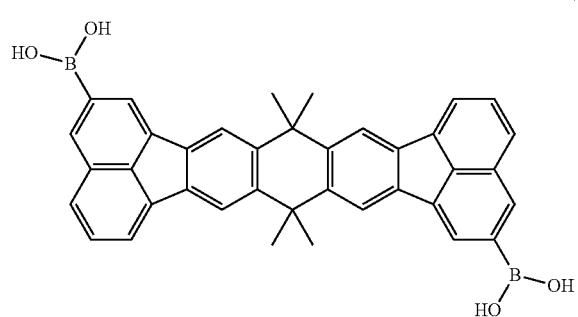
(60)
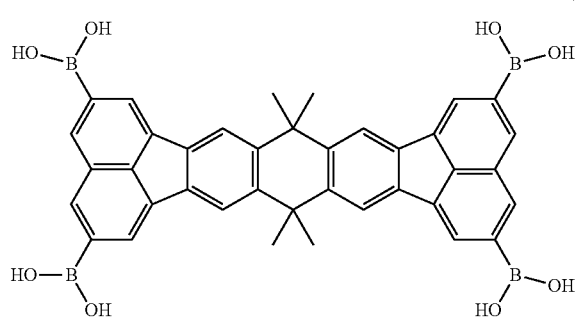
(61)
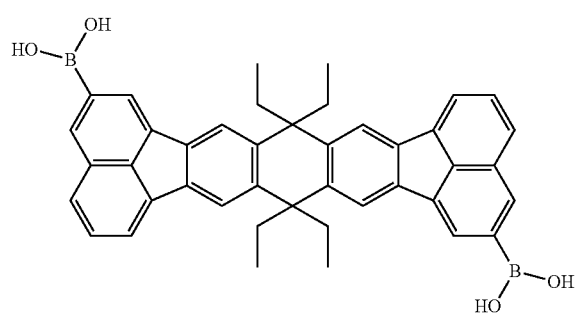
(62)
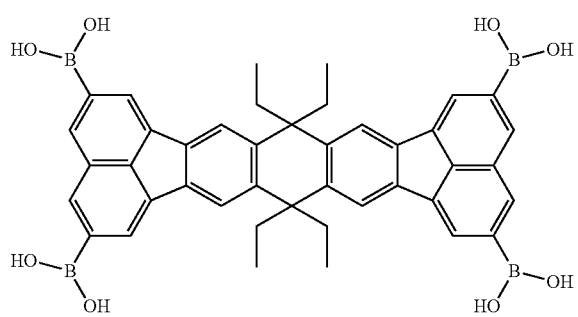
(63)

-continued

(64)
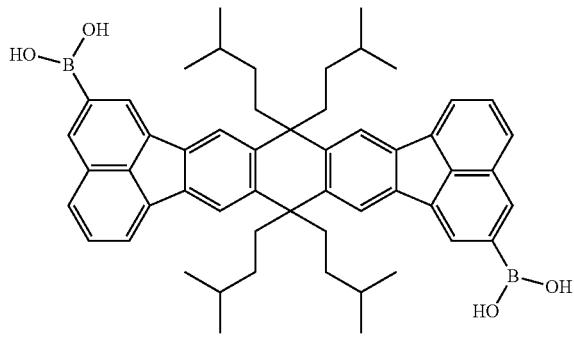

(65)
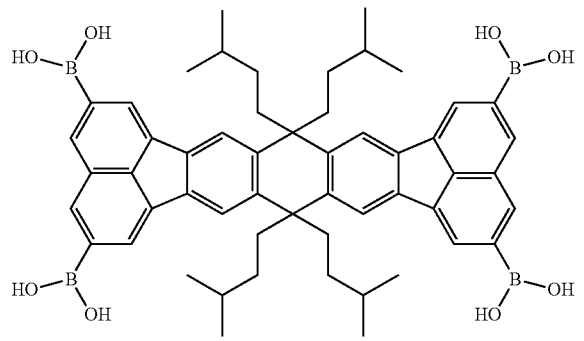

(66)
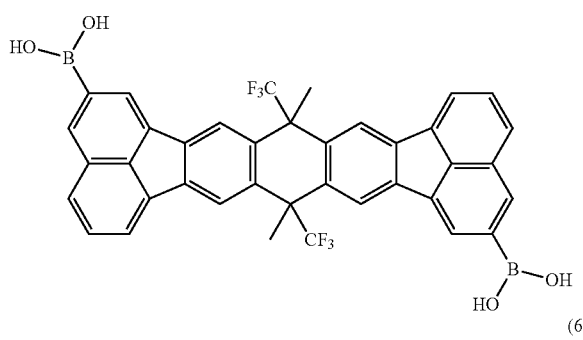

(67)
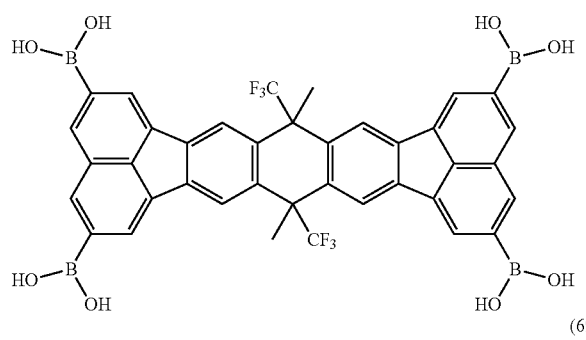

(68)
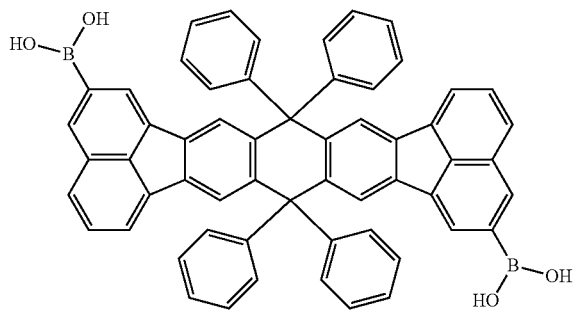

(69)
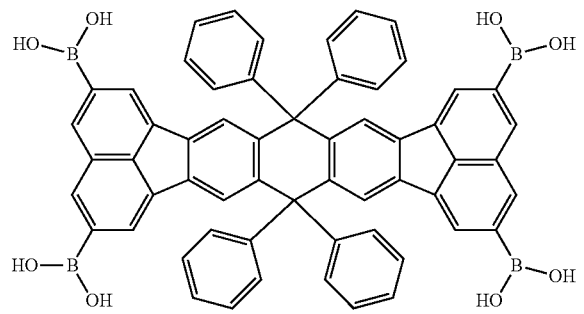

Hereinafter, an organic light emitting device of the present invention is described in detail.

The organic light emitting device of the present invention includes an anode, a cathode, and an organic compound layer interposed between the anode and the cathode.

Hereinafter, an organic light emitting device of the present invention is described in detail with reference to the drawings.

First, reference numerals in the figures are described. An organic light emitting device 1a, an organic light emitting device 1b, and an organic light emitting device 1c each include a metal electrode 10, an electron-injection transport layer 11, a light emitting layer 12, a hole-injection transport layer 13, a transparent electrode 14, a transparent substrate 15, an interlayer 16, and a hole blocking layer 17.

An image display apparatus 20 includes a scanning signal driver 21, an information signal driver 22, and a current supply source 23. A pixel circuit 30 includes a first thin film transistor (TFT1) 31, a capacitor ($C_{add}$) 32, a second thin film transistor (TFT2) 33, and a cathode 35.

A display apparatus 40 includes a substrate 41, a moisture-proof film 42, a gate electrode 43, a gate insulating film 44, a semiconductor film 45, a drain electrode 46, a source electrode 47, an insulating film 48, and a contact hole (through-hole) 49.

The display apparatus 40 further includes an anode 50, an organic compound layer 51, a cathode 52, a first protective layer 53, and a second protective layer 54.

Figure 1B:
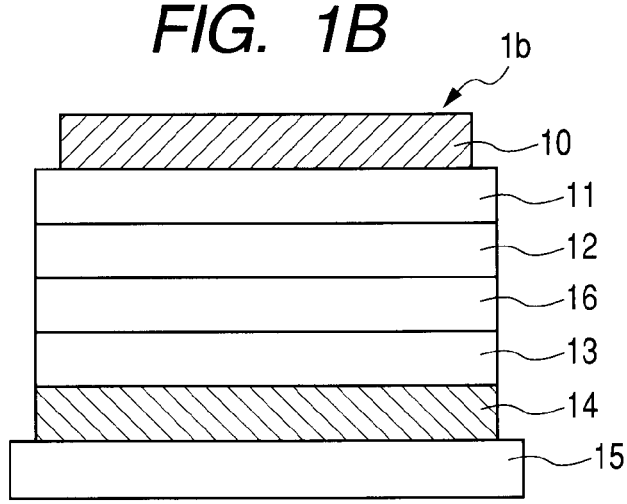
Figure 1C:
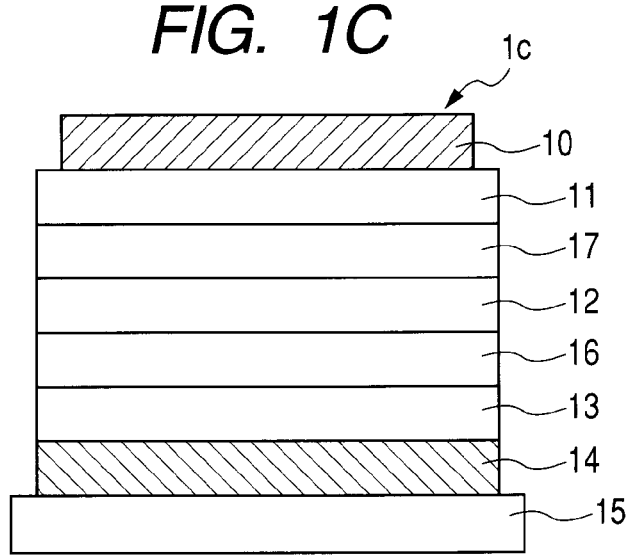

FIGS. 1A to 1C are cross-sectional views each illustrating an example of an embodiment of an organic light emitting device of the present invention.

FIG. 1A is a cross-sectional view illustrating a first embodiment of the organic light emitting device of the present invention. In an organic light emitting device 1a in FIG. 1A, a laminate in which the metal electrode 10, the electron-injection transport layer 11, the light emitting layer 12, the hole-injection transport layer 13, and the transparent electrode 14 are formed in the stated order from the top is provided on the transparent substrate 15.

The organic light emitting device 1a in FIG. 1A exhibits an electrical rectifying property. When an electric field is applied to the organic light emitting device 1a so that the metal electrode 10 functions as a cathode and the transparent electrode 14 functions as an anode, electrons are injected to the light emitting layer 12 from the metal electrode 10 and holes are injected to the light emitting layer 12 from the transparent electrode 14. The injected holes and electrons are recombined in the light emitting layer 12 to generate excitons, whereby the organic light emitting device emits light when the excitons return to a ground state. At this time, the hole-injection transport layer 13 also functions as a layer blocking electrons. This enhances the recombination efficiency of the holes and electrons at an interface between the light emitting layer 12 and the hole-injection transport layer 13, so an emission efficiency is enhanced.

FIG. 1B is a cross-sectional view illustrating a second embodiment of the organic light emitting device of the present invention. The organic light emitting device 1b in FIG. 1B corresponds to the organic light emitting device in FIG. 1A in which the interlayer 16 is provided between the light emitting layer 12 and the hole-injection transport layer 13. By providing the interlayer 16, the electrons moving from the light emitting layer 12 to the hole-injection transport layer 13 can be blocked effectively. Thus, the interlayer 16 may be referred to as an electron blocking layer. Further, the interlayer 16 also has an effect of blocking diffusion ions (including metallic ions) seeping from the transparent electrode 14 and the hole-injection transport layer 13. Therefore, the emission efficiency of a device is enhanced, and the durability is also enhanced.

FIG. 1C is a cross-sectional view illustrating a third embodiment of the organic light emitting device of the present invention. The organic light emitting device 1c in FIG. 1C corresponds to the organic light emitting device in FIG. 1B in which a hole blocking layer 17 is provided between the electron-injection transport layer 11 and the light emitting layer 12. By providing the hole blocking layer 17, a hole seeping from the light emitting layer 12 can be blocked effectively. In addition, the hole blocking layer 17 also has an effect of preventing the diffusion ions (including metallic ions) from diffusing to the light emitting layer 12 by blocking a diffusion ions seeping from the metal electrode 10 and the electron-injection transport layer 11. Accordingly, the hole blocking layer 17 may be referred to as a metal diffusion-preventing layer. From the foregoing, the emission efficiency of the organic light emitting device is improved and the durability is also improved.

It should be noted that the device structures according to FIGS. 1A to 1C are each merely very basic one, and the structure of the organic light emitting device of the present invention is not limited to those. For example, an insulating layer may be provided onto an interface between an electrode and an organic compound layer, an adhesive layer or an interference layer may be provided thereonto, and a hole-injection transport layer may be formed of two layers having different ionization potentials or energy band gaps. Thus, the organic light emitting device can be formed of various layers.

The organic light emitting device of the present invention includes at least one kind of the fused polycyclic aromatic compound of the present invention in at least one layer of the organic compound layers. Here, the organic compound layers specifically refer to the electron-injection transport layer 11, the light emitting layer 12, the hole-injection transport layer 13, the interlayer 16, and the hole blocking layer 17 illustrated in FIGS. 1A to 1C. In particular, the organic light emitting device is useful as the material for the light emitting layer 12, the electron-injection transport layer 13, or the hole-injection transport layer 11. In addition, the layer constituting the organic light emitting device of the present invention is formed by a vacuum vapor deposition method or a solution coating method, thereby becoming a layer which is hardly crystallized and has excellent stability with time.

When used as a constituent material for the light emitting layer 12, the fused polycyclic aromatic compound of the present invention can be used together with, as required, a known low-molecular-weight and polymer light emitting material, hole transporting material, or a electron transporting material.

The light emitting material includes, for example, a fluorescent light emitting material. Specific examples of the fluorescent light emitting material include benzooxazole and a derivative thereof, benzoimidazole and a derivative thereof, benzothiazole and a derivative thereof, styrylbenzene and a derivative thereof, polyphenyl and a derivative thereof, diphenylbutadiene and a derivative thereof, tetraphenylbutadiene and a derivative thereof, naphthalimide and a derivative thereof, coumarin and a derivative thereof, a fused polycyclic aromatic compound, perinone and a derivative thereof, oxadiazole and a derivative thereof, oxadine and a derivative thereof, aldazine and a derivative thereof, pyraridine and a derivative thereof, cyclopendadiene and a derivative thereof, bisstyryl anthracene and a derivative thereof, quinacridon and a derivative thereof, pyrrolopyridine and a derivative thereof, thiadiazoropyridine and a derivative thereof, cyclopentadiene and a derivative thereof, styrylamine and a derivative thereof, diketopyrrolopyrrole and a derivative thereof, an aromatic dimethylidene compound, 8-quinolinol and a metal complex that is a derivative thereof, pyrromethene and a metal complex that is a derivative thereof, a rare earth complex, various kinds of metal complexes such as a transition metal complex, polymer compounds such as polythiophene, polyphenylene, and polyphenylenevinylene, and an organic silane and a derivative thereof. Preferred is a fused polycyclic aromatic compound, a quinacridon derivative, diketopyrrolopyrole derivative, a metal complex of a pyrromethene derivative, a rare earth complex, or a transition metal complex, and more preferred is a fused polycyclic aromatic compound and a transition metal complex.

On the other hand, considering an emission efficiency (external quantum efficiency of an organic light emitting device), it is possible to use a phosphorescent material as the light emitting material.

The phosphorescent light emitting material is preferably a transition metal complex such as iridium, platinum, rhenium, or ruthenium, and more preferably a transition metal complex such as iridium or platinum.

Examples of the hole transporting material include triarylamine derivatives, phenylene diamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, porphyrin derivatives, poly(vinylcarbazole), poly(silylene), and poly(thiophene).

Further, examples of the electron transporting material include organic compounds such as oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and an organic metal complex such as a quinolinol aluminum complex.

When used as the constituent material for the electron-injection transport layer 11, the fused polycyclic aromatic compound of the present invention can be used in the presence of a known metal, metal salt, a metal oxide, or the like, as required.

Specific examples of the metal, metal salt, and metal oxide include metals such as lithium, sodium, potassium, cesium, calcium, magnesium, aluminum, indium, silver, lead, tin, and chromium, metal fluorides such as lithium fluoride and aluminum fluoride, and a metal carbonate such as cesium carbonate.

In the organic light emitting device of the present invention, a material which forms the anode has as large a work function as possible. Examples of available materials include: metal elements such as gold, silver, platinum, nickel, palladium, cobalt, selenium, and vanadium; alloys combining those metal elements; and metal oxides such as tin oxide, zinc oxide, indium tin oxide (ITO), and indium zinc oxide. Further, conductive polymers such as polyaniline, polypyrrole, polythiophene, and polyphenylene sulfide may also be used. One kind of those electrode substances may be used singly. Alternatively, two or more kinds of them may also be used in combination. Further, the anode may be formed of a single layer or multiple layers.

On the other hand, a material which forms the cathode has as small a work function as possible. Examples of available materials include: metal elements such as lithium, sodium, potassium, cesium, calcium, magnesium, aluminum, indium, silver, lead, tin, and chromium; alloys formed of multiple metal elements in combination; and salts thereof. Further, metal oxides such as indium tin oxide (ITO) may also be used. Further, the cathode may be formed of a single layer or multiple layers.

Substrates which is used in the organic light emitting device of the present invention include: opaque substrates such as metallic substrates and ceramics substrates; and transparent substrates such as glass, quartz, and plastic sheet substrates, but are not particularly limited to those materials. In addition, a color filter film, a fluorescent color converting film, a dielectric reflection film, or the like may be used in the substrate to control emitted light.

It is preferred that the organic light emitting device of the present invention be finally covered with a protective layer. As a material for the protective layer, those which have a function of preventing a substance that promotes the degradation in a device, such as water and oxygen, from entering the device may be used. Specific examples thereof include: metal elements such as In, Sn, Pb, Au, Cu, Ag, Al, Ti, and Ni; metal oxides such as MgO, SiO, $SiO_2$, $Al_2O_3$, GeO, NiO, CaO, BaO, $Fe_2O_3$, $Y_2O_3$, and $TiO_2$; metal fluorides such as $MgF_2$, LiF, $AlF_3$, and $CaF_2$; nitrides such as $SiN_x$ and $SiO_xN_y$; polyethylene; polypropylene; polymethylmethacrylate; polyimide; polyurea; polytetrafluoroethylene; polychlorotrifluoroethylene; polydichlorodifluoroethylene; a copolymer of chlorotrifluoroethylene and dichlorodifluoroethylene; a copolymer obtained by copolymerizing a monomer mixture containing tetrafluoroethylene and at least one kind of comonomer; a fluorene-containing copolymer having a cyclic structure in a copolymer main chain; a water-absorbing material with a water-absorbing ratio of 1% or more; and a moisture-proof material with a water-absorbing ratio of 0.1% or less.

There is no particular limit to the method of forming a protective layer covering the organic light emitting device, and for example, a vacuum vapor deposition method, a sputtering, a reactive sputtering, a molecular beam epitaxy (MBE) method, a cluster ion beam method, an ion plating, a plasma polymerization (high-frequency excitation ion plating), a plasma CVD, a laser CVD, a thermal CVD, a gas source CVD, a coating, a printing, and a transfer method can be applied.

In the organic light emitting device of the present invention, as a layer containing the fused polycyclic aromatic compound of the present invention, a thin film is generally formed by a vacuum vapor deposition method, or a coating method involving being dissolved in an appropriate solvent. Specific examples of the method of forming a thin film by a coating method include a spin coating, a slit coater method, a printing, an ink-jet method, and a spray method. Among the fused polycyclic aromatic compounds of the present invention, a compound having a molecular weight exceeding 2,000 tends to have a high sublimation temperature. Therefore, in such a case, a thin film is preferably formed by the coating method.

In the case of forming a thin film by a coating method, it is necessary to prepare an ink composition containing the fused polycyclic aromatic compound of the present invention and a solvent. Examples of the solvents used in the ink composition include toluene, xylene, mesitylene, dioxane, tetralin, methylnaphthalene, tetrahydrofuran, and diglyme.

In the ink composition of the present invention, the amount of a solid component containing the fused polycyclic aromatic compound of the present invention is preferably 0.05% by weight or more and 20% by weight or less, and more preferably 0.1% by weight or more and 10% by weight or less with respect to the total weight of the ink composition. When the amount is smaller than 0.05% by weight, the concentration of the solid component in ink is extremely small, so the stability of a produced film may be impaired. When the amount is larger than 10% by weight, the solid component in ink may be precipitated without being dissolved completely, and a produced film may be enlarged in thickness.

In the organic light emitting device of the present invention, a light extraction efficiency, a color purity, and the like can be enhanced due to various known means. For example, by processing the shape of a substrate surface (for example, form a fine uneven pattern), controlling the refractive indices of a substrate/an ITO layer/an organic layer, controlling the thicknesses of a substrate/an ITO layer/an organic layer, and the like, the light extraction efficiency and the external quantum efficiency can be enhanced. Also, a color purity can be enhanced by reducing an excessive wavelength component using a micro-cavity structure (micro resonator structure), obtaining a desired color with a color filter, and the like.

The organic light emitting device of the present invention may be a so-called top emission system in which light is extracted from an anode side for the purpose of enhancing an opening ratio, or a cavity structure of adjusting the color purity by optical buffer.

The organic light emitting device of the present invention is applicable to a product which requires energy conservation and high luminance. As application examples, an image display apparatus, a light source of a printer, an illumination apparatus, a backlight of a liquid crystal display apparatus, and the like are conceivable.

An example of the image display apparatus includes an energy-efficient and light-weight flat panel display with high visibility.

Further, as the light source of a printer, for example, a laser light source portion of a laser beam printer that has been currently used widely can be replaced by the organic light emitting device of the present invention. An example of a replacement method includes a method of placing an organic light emitting device that can be addressed independently on an array. Even if the laser light source portion is replaced by the organic light emitting device of the present invention, there is no particular difference in the formation of an image from a conventional example by conducting desired light exposure to a photosensitive drum. The volume of an apparatus can be reduced remarkably by using the organic light emitting device of the present invention.

Regarding the illumination apparatus and the backlight, the effect of saving energy can be expected by using the organic light emitting device of the present invention.

Next, the display apparatus of the present invention is described. The display apparatus of the present invention uses the organic light emitting device of the present invention. Hereinafter, the display apparatus of the present invention is described in detail by exemplifying an active matrix system with reference to the drawings.

Figure 2:
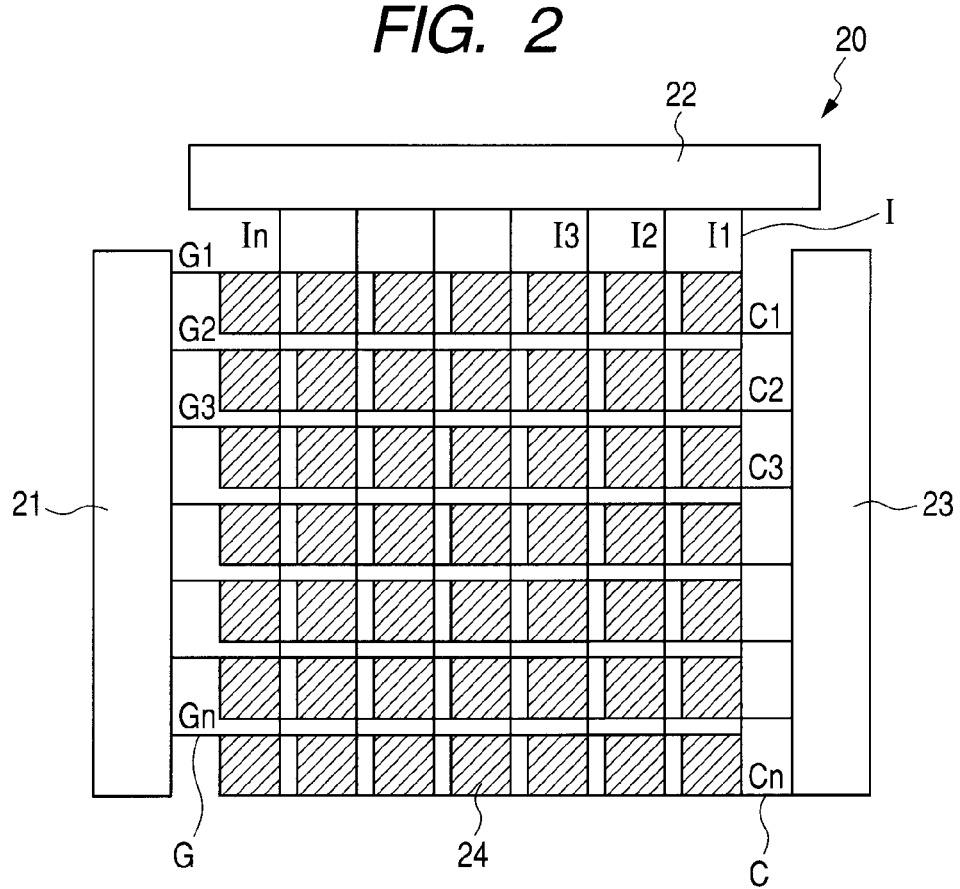
FIG. 2 is a view schematically illustrating an exemplary constitution of an image display apparatus provided with an organic light emitting device and a driving unit of the present invention.

FIG. 2 is a view schematically illustrating a configuration example of an image display apparatus including the organic light emitting device of the present invention and a driving unit. In an image display apparatus 20 illustrated in FIG. 2, a scanning signal driver 21, an information signal driver 22, and a current supply source 23 are placed, which are each connected to gate selection lines G, information signal lines I, or current supply lines C. A pixel circuit is placed at a crossing point of the gate selection line G and the information signal line I. The scanning signal driver 21 successively selects gate selection lines G1, G2, G3, . . . Gn, and in synchronization therewith, an image signal is applied from the information signal driver 22.

Figure 3:
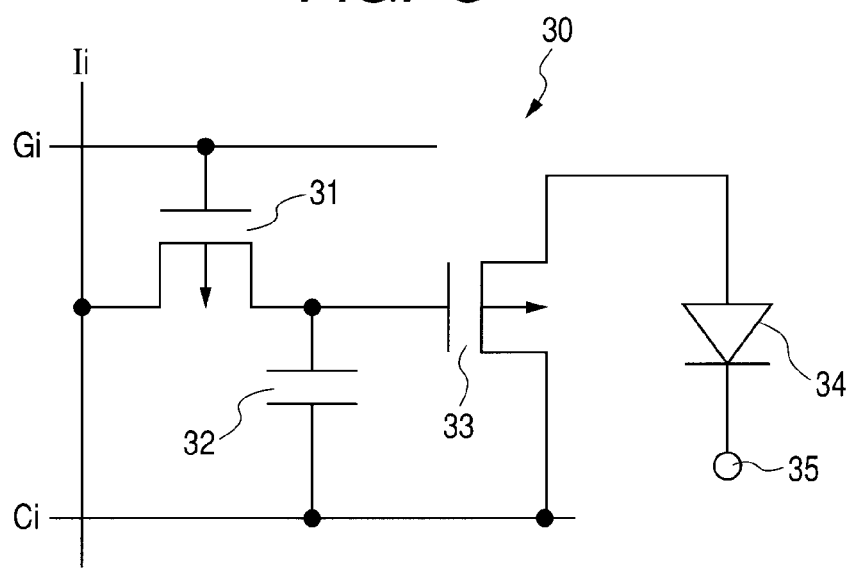
FIG. 3 is a circuit diagram showing a circuit constituting one pixel placed in the display apparatus illustrated in FIG. 2.

Next, the behavior of the pixels is described. FIG. 3 is a circuit diagram illustrating a circuit constituting one pixel placed in the image display apparatus in FIG. 2. In a pixel circuit 30 in FIG. 3, when a selection signal is applied to the gate selection line G, a first thin film transistor (TFT1) 31 is turned on, and an image signal is supplied to a capacitor ($C_{add}$) 32, whereby a gate voltage of a second thin film transistor (TFT2) 33 is determined. A current is supplied to an organic light emitting device 34 from a current supply line C in accordance with a gate voltage of the second thin film transistor 33. The gate potential of the second thin film transistor 33 is held at the capacitor 32 until the first thin film transistor 31 is scanned and selected next. Therefore, a current continues to flow through the organic light emitting device 34 until the subsequent scanning is conducted. This enables the organic light emitting device 34 to emit light at all times during one frame.

Figure 4:
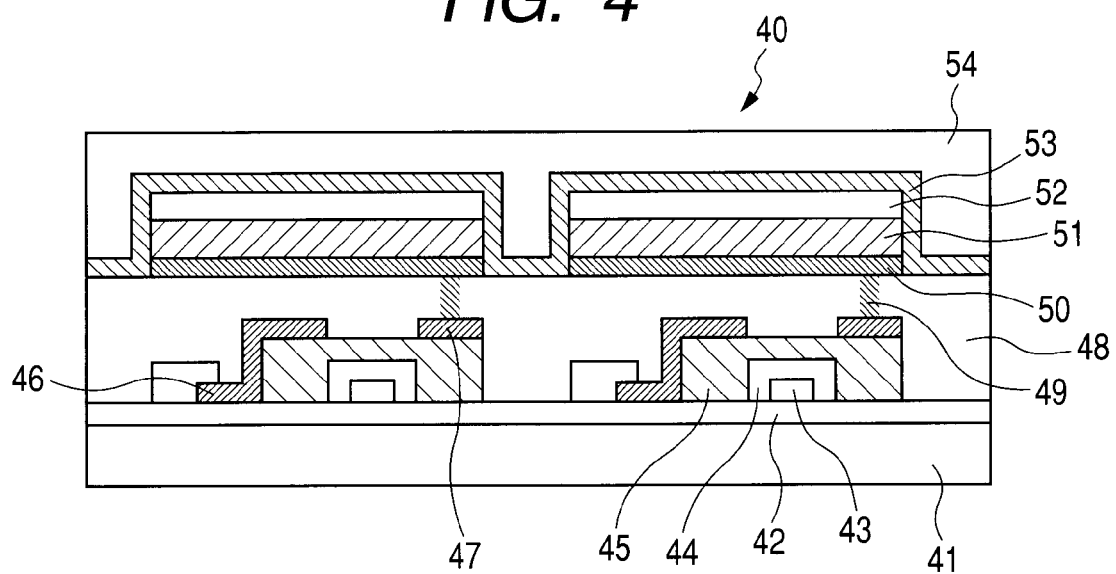
FIG. 4 is a cross-sectional schematic view illustrating one embodiment of the display apparatus of the present invention.

FIG. 4 is a cross-sectional schematic view illustrating one embodiment of the display apparatus of the present invention. In FIG. 4, the detail of the configuration of a display apparatus 40 is described by way of an example of the production process of the display apparatus 40. In the display apparatus 40, a substrate 41 formed of glass or the like is coated with a moisture-proof film 42 for protecting a member (TFT or organic compound layer) formed in an upper portion of the substrate 41. As a coating material serving as a constituent material of the moisture-proof film 42, silicon oxide, a composite of silicon oxide and silicon nitride, or the like is used. Next, metal such as Cr is formed into a film by sputtering and patterned to a predetermined circuit shape, whereby a gate electrode 43 is formed. Subsequently, silicon oxide or the like is formed into a film by a plasma CVD, a catalyst chemical vapor deposition (cat-CVD), or the like, and patterned to form a gate insulating film 44. Next, a silicon film is produced by a plasma CVD (by annealing at a temperature of 290° C. or higher in some cases), and patterned in accordance with a circuit shape, whereby a semiconductor layer 45 is formed.

Further, a drain electrode 46 and a source electrode 47 are each provided on the semiconductor layer 45 to produce a TFT element, whereby a pixel circuit 30 as illustrated in FIG. 3 is formed. Next, an insulating film 48 is formed in an upper portion of the TFT element. After that, a contact hole (through-hole) 49 is formed so that a lower electrode (anode) 50 for an organic light emitting device formed of metal comes into contact with a source electrode 47.

A multi-layer or signal-layer organic compound layer 51 and a cathode 52 are successively laminated on the anode 50, whereby a display apparatus can be obtained. Note that, in order to protect the organic light emitting device from water and oxygen in the atmosphere, a first protective layer 54 and a second protective layer 55 may be preferably provided. By driving the display apparatus using the fused polycyclic aromatic compound of the present invention, a display of a satisfactory quality, which is stable for a display for a long period of time, can be conducted.

In the display apparatus of the present invention, there is no particular limit to a switching element, and any switching element can be easily applied to a single crystal silicon substrate, an MIM element, an a-Si type, and the like.

EXAMPLES

Hereinafter, the present invention is described more specifically by way of examples, but the present invention is not limited thereto.

Example 1

Synthesis of Exemplified Compound [1]

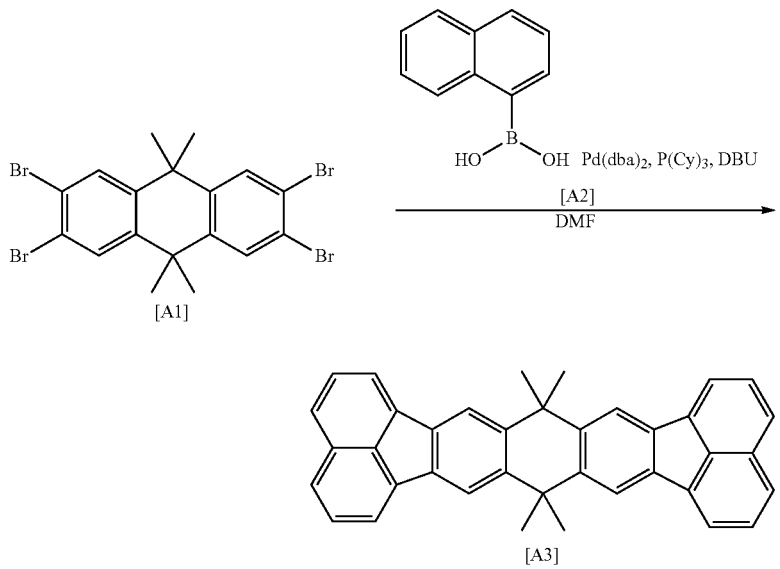

The following reagents and solvents were loaded into a 300-ml three-necked flask and the inside of the flask was set to a nitrogen atmosphere.

| | |
|---|---|
| Compound (A1): | 1 g (1.8 mmol) |
| Compound (A2): | 0.75 g (4.3 mmol) |
| Pd(dba)$_2$ (bis(benzylidene acetone) palladium catalyst): | 0.75 g (0.7 mmol) |
| P(Cy)$_3$: | 0.82 g (2.9 mmol) |
| Dehydrated dimethyl formamide: | 100 ml |

Next, the reaction solution was heated to 155° C., and thereafter, stirred at the temperature for 9 hours. After the completion of the reaction, a precipitate was filtered and dissolved in chloroform. Then, a column purification (filler: silica gel, developing solvent: chloroform) was carried out and the solvent was distilled off under reduced pressure. Next, the resultant was recrystallized with chloroform, whereby 112 mg (yield 11.8%) of Compound (A3) of interest (Exemplified Compound [1]) was obtained.

Example 2

Synthesis of Exemplified Compound (51)

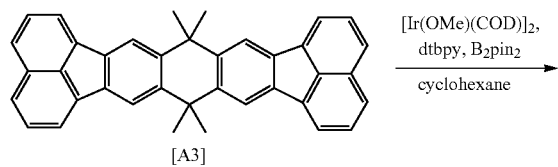

[A3]

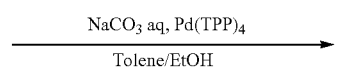

[B1]

The following reagents and solvents were loaded into a 300-ml three-necked flask and the inside of the flask was set to a nitrogen atmosphere.

| | |
|---|---|
| Compound (A3): | 1.94 g (4.0 mmol) |
| B$_2$pin$_2$ (bispinacolborane): | 2.86 g (17 mmol) |
| [Ir(OMe)(COD)]$_2$ (biscyclooctadiene(methoxy) palladium catalyst): | 0.14 g (0.12 mmol) |
| dtbpy (ditertiary-butyl-2,2'-bipyridine): | 0.04 g (0.16 mmol) |
| Cyclohexane: | 100 ml |

Next, the reaction solution was heated to 80° C., and thereafter, stirred at the temperature for 27 hours. After the completion of the reaction, the solvent was distilled off under reduced pressure, whereby a crude product was obtained. Next, the obtained crude product was subjected to a column purification (filler: silica gel, developing solvent: heptane/chloroform=1/1). Next, the resultant was recrystallized with a mixed solvent of chloroform/methanol, whereby 1.3 g (yield 32.8%) of Compound (B1) of interest (Exemplified Compound (51)) was obtained.

Example 3

Synthesis of Exemplified Compound (15)

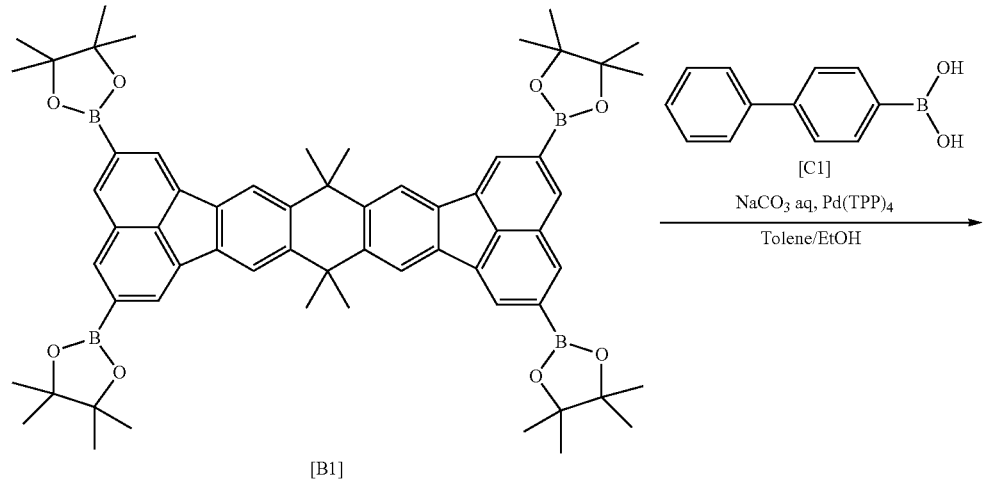

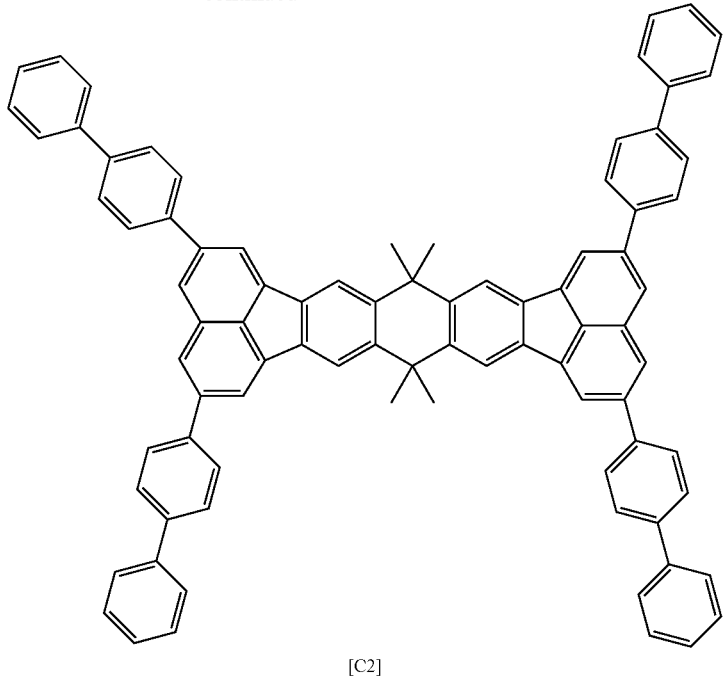

[C2]

The following reagents and solvents were loaded into a 200-ml three-necked flask and the inside of the flask was set to a nitrogen atmosphere.

| Compound (B1): | 1.0 g (1.0 mmol) |
| Borane compound (C1): | 0.83 g (4.2 mmol) |
| Toluene: | 40 ml |
| Ethanol: | 10 ml |

While the reaction solution was stirred at room temperature, 12 ml of an aqueous solution of saturated sodium carbonate were dropped thereto. Next, 0.23 g (0.2 mmol) of Pd(TPP)$_4$ [tetrakis(tripihenyl phosphine)palladium(0)) was added thereto. Next, after the reaction solution was stirred at room temperature for 30 minutes, the reaction solution was further stirred for 24 hours while being refluxed. After the completion of the reaction, an organic layer was extracted with chloroform and the solvent was distilled off under reduced pressure, whereby a crude product was obtained. Next, the obtained crude product was purified by silica gel column chromatography (developing solvent: mixed solvent of hexane and chloroform), whereby 0.35 g (yield 31.8%) of Compound (C2) (Exemplified Compound (15)) as a white solid was obtained.

Example 4

Synthesis of Exemplified Compound (24)

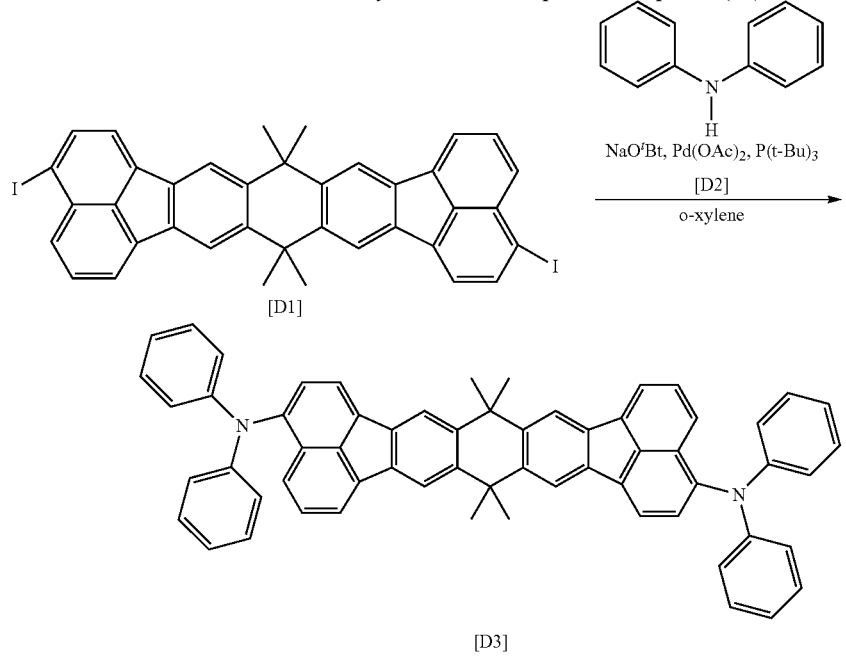

The following reagents and solvents were loaded into a 500-ml three-necked flask and the inside of the flask was set to a nitrogen atmosphere.

| Compound (D1): | 1 g (15.4 mmol) |
|---|---|
| o-xylene: | 250 ml |

Next, the following reagents and solvents were loaded thereto.

| Compound (D2): | 6.5 g (38.5 mol) |
|---|---|
| Sodium-t-butoxide: | 3.7 g |
| Palladium acetate: | 0.68 g |
| Tri(t-butoxy)phosphine: | 2.5 g |

Next, the reaction solution was heated to 120° C. and stirred at the temperature for 5 hours. After the completion of the reaction, the solvent was distilled off under reduced pressure, whereby a crude product was obtained. Next, the obtained crude product was purified by silica gel column chromatography (developing solvent: hexane), whereby 3.8 g (yield 80%) of Compound (D3) (Exemplified Compound (24)) was obtained.

Example 5

Synthesis of Exemplified Compound (34)

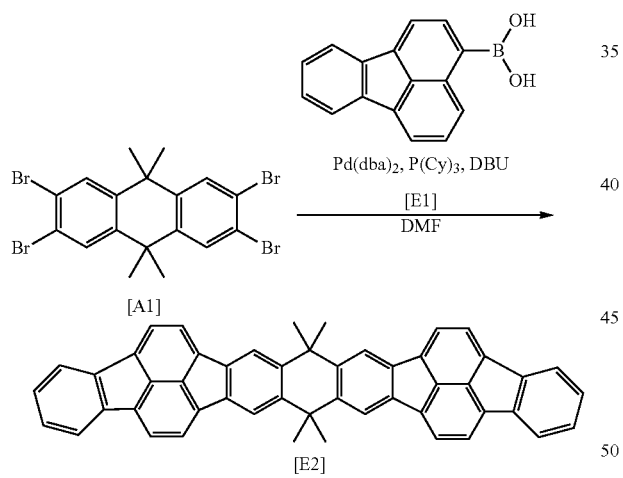

The following reagents and solvents were loaded into a 300-ml three-necked flask and the inside of the flask was set to a nitrogen atmosphere.

| Compound (A1): | 1 g (1.8 mmol) |
|---|---|
| Compound (E1): | 1.05 g (4.3 mmol) |
| Pd(dba)$_2$ (bis(benzylidene acetone) palladium catalyst): | 0.75 g (0.7 mmol) |
| P(Cy)$_3$: | 0.82 g (2.9 mmol) |
| Dehydrated dimethyl formamide: | 100 ml |

Next, the reaction solution was heated to 155° C., and stirred at the temperature for 24 hours. After the completion of the reaction, a precipitate was filtered and dissolved in chloroform. Then, a column purification (filler: silica gel, developing solvent: chloroform) was carried out and the solvent was distilled off under reduced pressure. Next, the resultant was recrystallized with chloroform, whereby 255 mg (yield 22.2%) of Compound (E2) of interest (Exemplified Compound (34)) was obtained.

Example 6

Production of Organic Light Emitting Device

An organic light emitting device having a structure illustrated in FIG. 1A was produced. Note that, in this example, the fused polycyclic aromatic compound was contained in the light emitting layer.

First, as a transparent electrode 14, a film of indium tin oxide (ITO) was formed on a glass substrate (transparent substrate 15) by sputtering. In this time, the film thickness of the transparent electrode 14 was set to 120 nm. Next, the substrate was subjected to ultrasonic cleaning sequentially with acetone and isopropyl alcohol (IPA). Then, the resultant was washed in boiling IPA, followed by drying. Further, the resultant was subjected to UV/ozone cleaning. The thus-treated substrate was used as a transparent conductive supporting substrate.

On the transparent conductive supporting substrate, α-NPD [N,N'-bis(1-naphthyl)-N,N'-diphenyl[1,1'-biphenyl]-4,4'-diamine] represented below was formed into a film by a vacuum vapor deposition method, whereby a hole-injection transport layer 13 was formed. In this time, the thickness of the hole-injection transport layer 13 was 30 nm. The vacuum degree was $1.0 \times 10^{-4}$ Pa and the vapor deposition rate was 0.2 nm/sec to 0.4 nm/sec.

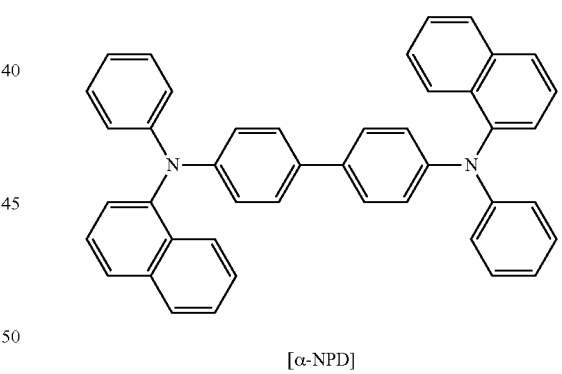

[α-NPD]

Next, on the hole-injection transport layer 13, Compound (A3) ((Exemplified Compound [1]) synthesized in Example 1 was formed into a film by a vacuum vapor deposition method, whereby a light emitting layer 12 was formed. In this time, the thickness of the light emitting layer 12 was 30 nm. The vacuum degree was $1.0 \times 10^{-4}$ Pa and the vapor deposition rate was 0.2 nm/sec to 0.4 nm/sec.

Next, on the light emitting layer 12, Alq$_3$ (8-hydroxyqunoline aluminum) represented below was formed into a film by a vacuum vapor deposition method, whereby an electron-injection transport layer 11 was formed. In this time, the thickness of the electron-injection transport layer 11 was 20 nm. The vacuum degree was $1.0 \times 10^{-4}$ Pa and the vapor deposition rate was 0.2 nm/sec to 0.4 nm/sec.

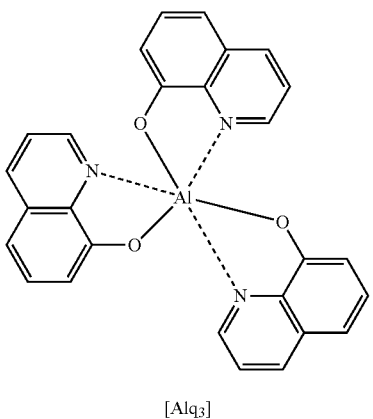

[Alq3]

Next, on the electron-injection transport layer 11, LiF (lithium fluoride) was formed into a film by a vacuum vapor deposition method, whereby an LiF film was formed. In this time, the thickness of the LiF film was 0.5 nm. The vacuum degree was $1.0\times10^{-4}$ Pa and the film formation rate was 0.1 nm/sec. Next, on the LiF film, Al was formed into a film by a vacuum vapor deposition method, whereby an Al film was formed. In this time, the thickness of the Al film was 120 nm. The vacuum degree was $1.0\times10^{-4}$ Pa and the film formation rate was 1.0 nm/sec or more and 1.2 nm/sec or less. Note that the LiF film and the Al film each function as a metal electrode 10.

Finally, the layers were covered with a protection glass plate under a nitrogen atmosphere and sealed with an acrylic adhesive material. Thus, an organic light emitting device was obtained.

When a DC voltage was applied to the obtained device by using an ITO electrode (transparent electrode 14) as a positive electrode and an Al electrode (metal electrode 10) as a negative electrode, the device showed a blue light emission. In addition, when a driving voltage was set to 5 V, the emission luminance was 750 cd/m$^2$.

In addition, a constant current driving test (durability test) was carried out while the initial luminance was set to 200 cd/m$^2$. In this time, the time required for the emission luminance to attenuate to the half of the initial luminance (luminance half time) was 520 hours.

Comparative Example 1

An organic light emitting device was produced in the same way as in Example 6 except that a fluoranthene (manufactured by Sigma-Aldrich) represented below instead of Compound (A3) (Exemplified Compound [1]) was formed into a film to form a light emitting layer 12 in Example 6. Note that, immediately after the fluoranthene represented below was formed into a film, whitening of the film was observed.

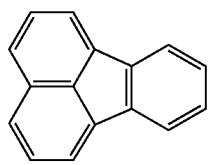

[Fluoranthene]

When a DC voltage was applied to the obtained device by using the ITO electrode (transparent electrode 14) as a positive electrode and the Al electrode (metal electrode 10) as a negative electrode, the device showed a blue light emission. In addition, when a driving voltage was set to 5 V, the emission luminance was 120 cd/m$^2$.

In addition, a constant current driving test was carried out in the same way as in Example 6, the luminance half time was 5 hours.

Example 7

An organic light emitting device was produced in the same way as in Example 6 except that Compound (D3) (Exemplified Compound (24)) instead of Compound (A3) (Exemplified Compound [1]) was formed into a film to form a light emitting layer 12 in Example 6.

When a DC voltage was applied to the obtained device by using the ITO electrode (transparent electrode 14) as a positive electrode and the Al electrode (metal electrode 10) as a negative electrode, the device showed a blue-green light emission. In addition, when a driving voltage was set to 5 V, the emission luminance was 3,200 cd/m$^2$.

In addition, a constant current driving test (durability test) was carried out while the initial luminance was set to 1,000 cd/m$^2$. In this time, the time required for the emission luminance to attenuate to the half of the initial luminance (luminance half time) was 980 hours.

Comparative Example 2

An organic light emitting device was produced in the same way as in Example 6 except that N,N-di(methylphenyl)-3-fluoranthene instead of Compound (A3) (Exemplified Compound [1]) was formed into a film to form a light emitting layer 12 in Example 6. Note that N,N-di(methylphenyl)-3-fluoranthene below was a compound described in Japanese Patent Application Laid-Open No. 2002-043058 and a compound obtained according to a synthesis method described in the application.

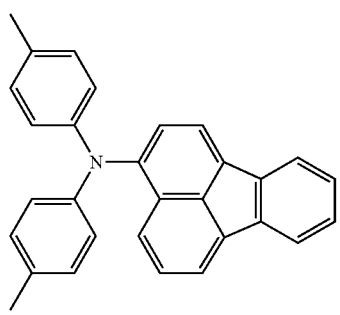

[N,N-di(methylphenyl)-3-fluoranthene]

When a DC voltage was applied to the obtained device by using the ITO electrode (transparent electrode 14) as a positive electrode and the Al electrode (metal electrode 10) as a negative electrode, the device showed a blue-green light emission. In addition, when a driving voltage was set to 5 V, the emission luminance was 1,200 cd/m$^2$.

In addition, a constant current driving test was carried out in the same way as in Example 7, the luminance half time was 46 hours.

Example 8

An organic light emitting device was produced in the same way as in Example 6 except that Compound (C2) (Exemplified Compound (57)) instead of Compound (A3) (Exemplified Compound [1]) and Ir(piq)$_3$ (tris(phenylisoquinolin)iridium complex) were co-deposited to form a light emitting layer 12 in Example 6. Note that Ir(piq)$_3$ used in this example is a compound obtained in reference to a synthesis method described in Journal of American Chemical Society, 123, 4304 (2001). In addition, the vapor deposition rate ratio of Compound (C2) and Ir(piq)$_3$ was as follows: Compound (C2)/Ir(piq)$_3$=4/1.

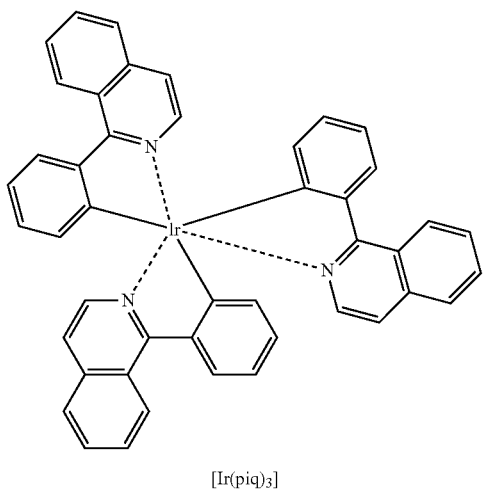

[Ir(piq)$_3$]

When a DC voltage was applied to the obtained device by using the ITO electrode (transparent electrode 14) as a positive electrode and the Al electrode (metal electrode 10) as a negative electrode, the device showed a red light emission. In addition, when a driving voltage was set to 5 V, the emission luminance was 800 cd/m$^2$.

In addition, a constant current driving test (durability test) was carried out while the initial luminance was set to 600 cd/m$^2$. In this time, the time required for the emission luminance to attenuate to the half of the initial luminance (luminance half time) was 855 hours.

Example 9

An organic light emitting device was produced in the same way as in Example 8 except that Compound (E2R) (Exemplified Compound (34)) synthesized in Example 5 was used instead of Compound (C2) (Exemplified Compound (57)) in Example 8 to form a light emitting device.

When a DC voltage was applied to the obtained device by using the ITO electrode (transparent electrode 14) as a positive electrode and the Al electrode (metal electrode 10) as a negative electrode, the device showed a red light emission. In addition, when a driving voltage was set to 5 V, the emission luminance was 850 cd/m$^2$.

In addition, a constant current driving test was carried out in the same way as in Example 8, the luminance half time was 760 hours.

Example 10

Production of Organic Light Emitting Device

An organic light emitting device having a structure illustrated in FIG. 1C was produced. Note that the fused polycyclic aromatic compound of the present invention is contained in the hole blocking layer.

First, as a transparent electrode 14, a film of indium tin oxide (ITO) was formed on a glass substrate (transparent substrate 15) by sputtering. In this time, the film thickness of the transparent electrode 14 was set to 120 nm. Next, the substrate was subjected to ultrasonic cleaning sequentially with acetone and isopropyl alcohol (IPA). Then, the resultant was washed in boiling IPA, followed by drying. Further, the resultant was subjected to UV/ozone cleaning. The thus-treated substrate was used as a transparent conductive supporting substrate.

On the transparent conductive supporting substrate, CuPc (phthalocyanine copper complex) was formed into a film by a vacuum vapor deposition method, whereby a hole-injection transport layer 13 was formed. In this time, the thickness of the hole-injection transport layer 13 was 5 nm. The vacuum degree was $1.0\times10^{-4}$ Pa and the vapor deposition rate was 0.2 nm/sec.

Next, on the hole-injection transport layer 13, α-NPD was formed into a film by a vacuum vapor deposition method, whereby an interlayer 16 was formed. In this time, the thickness of the interlayer 16 was 30 nm. The vacuum degree was $1.0\times10^{-4}$ Pa and the vapor deposition rate was 0.2 nm/sec to 0.4 nm/sec.

Next, on the interlayer 16, Alq$_3$ was formed into a film by a vacuum vapor deposition method, whereby a light emitting layer 12 was formed. In this time, the thickness of the light emitting layer 12 was 20 nm. The vacuum degree was $1.0\times10^{-4}$ Pa and the vapor deposition rate was 0.2 nm/sec to 0.4 nm/sec.

Next, on the light emitting layer 12, Compound (A3) (Exemplified Compound [1]) synthesized in Example 1 was formed into a film by a vacuum vapor deposition method, whereby a hole blocking layer 17 was formed. In this time, the thickness of the hole blocking layer 17 was 20 nm. The vacuum degree was $1.0\times10^{-4}$ Pa and the vapor deposition rate was 0.2 nm/sec to 0.4 nm/sec.

Next, on the hole blocking layer 17, Alq$_3$ was formed into a film by a vacuum vapor deposition method, whereby an electron-injection transport layer 11 was formed. In this time, the thickness of the electron-injection transport layer 11 was 20 nm. The vacuum degree was $1.0\times10^{-4}$ Pa and the vapor deposition rate was 0.2 nm/sec to 0.4 nm/sec.

Next, on the electron-injection transport layer 11, LiF (lithium fluoride) was formed into a film by a vacuum vapor deposition method, whereby an LiF film was formed. In this time, the thickness of the LiF film was 0.5 nm. The vacuum degree was $1.0\times10^{-4}$ Pa and the film formation rate was 0.1 nm/sec. Next, on the LiF film, Al was formed into a film by a vacuum vapor deposition method, whereby an Al film was formed. In this time, the thickness of the Al film was 120 nm. The vacuum degree was $1.0\times10^{-4}$ Pa and the film formation rate was 1.0 nm/sec or more and 1.2 nm/sec or less. Note that the LiF film and the Al film each function as a metal electrode 10.

Finally, the layers were covered with a protection glass plate under a nitrogen atmosphere and sealed with an acrylic adhesive material. Thus, an organic light emitting device was obtained.

When a DC voltage was applied to the obtained organic light emitting device by using an ITO electrode (transparent electrode 14) as a positive electrode and an Al electrode (metal electrode 10) as a negative electrode, the device showed a green light emission. In addition, when a driving voltage was set to 5 V, the emission luminance was 3,500 cd/m².

In addition, a constant current driving test (durability test) was carried out while the initial luminance was set to 1,000 cd/m². In this time, the time required for the emission luminance to attenuate to the half of the initial luminance (luminance half time) was 680 hours.

Comparative Example 3

An organic light emitting device was produced in the same was as in Examples 10 except that the formation of the hole blocking layer 17 was omitted and the thickness of the electron-injection transport layer 11 was set to 40 nm in Example 10.

When a DC voltage was applied to the obtained organic light emitting device by using the ITO electrode (transparent electrode 14) as a positive electrode and the Al electrode (metal electrode 10) as a negative electrode, the device showed a green light emission. In addition, when a driving voltage was set to 5 V, the emission luminance was 1,800 cd/m².

In addition, a constant current driving test was carried out in the same way as in Example 10, the luminance half time was 55 hours.

From comparison between Example 10 and Comparative Example 3, it was confirmed that the hole injected from the anode side was blocked in the hole blocking layer 17 and sealed in the light emitting layer 12 in Example 10, with the result that high luminance could be obtained. On the other hand, in Comparative Example 1, the constituent material for the light emitting layer 12 and the constituent material for the electron-injection transport layer 11 are the same with each other. In this case, because the effect of blocking the hole (effect of sealing a carrier in the light emitting layer) is small, high luminance could not be obtained. In addition, it was highly possible that difference in efficiency of the device influenced the durability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-182216, filed Jul. 14, 2008, which is hereby incorporated by reference herein in its entirety.

The invention claimed is:

1. A fused polycyclic aromatic compound represented by the following general formula [1],

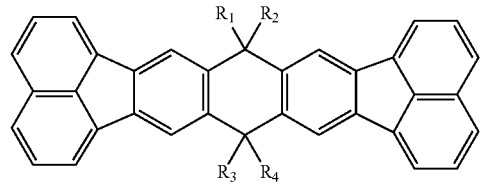

where $R_1$ to $R_4$ each represent hydrogen, a halogen atom, a substituted or unsubstituted alkyl group, a substituted or unsubstituted aralkyl group, or a substituted or unsubstituted aryl group.

2. A fused polycyclic aromatic compound represented by the following general formula [2],

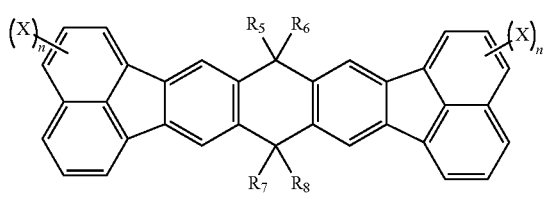

where: $R_5$ to $R_8$ each represent hydrogen, a halogen atom, a substituted or unsubstituted alkyl group, a substituted or unsubstituted aralkyl group, or a substituted or unsubstituted aryl group; X represents a substituted or unsubstituted alkyl group, a substituted or unsubstituted aralkyl group, a substituted or unsubstituted aryl group, a substituted or unsubstituted heterocyclic group, a substituted amino group, a substituted boryl group, a substituted silyl group, a cyano group, or a halogen atom; and n represents an integer of 0 to 6, and when n represents 2 or more, a plurality of X's may be the same as or different from each other and the plurality of X's may bond to each other to form a ring structure.

3. A fused polycyclic aromatic compound according to claim 2, wherein the fused polycyclic aromatic compound is synthesized by using, as a raw material, one of the compounds represented by the following general formulae [3] and [4],

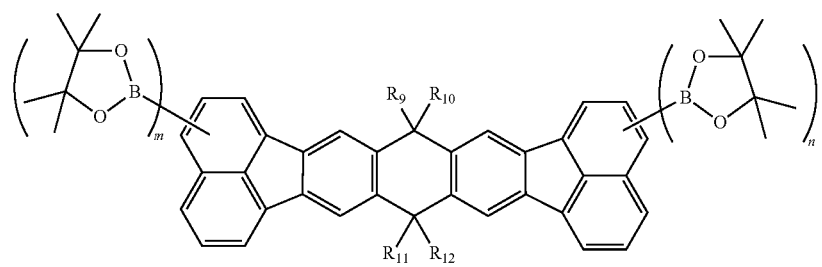

-continued

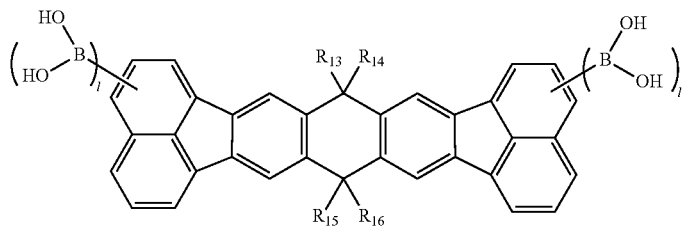

[4]

where: $R_9$ to $R_{12}$ each represent hydrogen, a halogen atom, a substituted or unsubstituted alkyl group, a substituted or unsubstituted aralkyl group, or a substituted or unsubstituted aryl group; and m represents an integer of 1 to 6, and where: $R_{13}$ to $R_{16}$ each represent hydrogen, a halogen atom, a substituted or unsubstituted alkyl group, a substituted or unsubstituted aralkyl group, or a substituted or unsubstituted aryl group; and l represents an integer of 1 to 6.

4. An organic light emitting device, comprising:
an anode;
a cathode;
an organic compound layer interposed between the anode and the cathode, wherein at least one layer of the organic compound layers includes at least one kind of the fused polycyclic aromatic compound according to claim 1.

5. A display apparatus comprising the organic light emitting device according to claim 4.

6. An organic light emitting device, comprising:
an anode;
a cathode;
an organic compound layer interposed between the anode and the cathode, wherein at least one layer of the organic compound layers includes at least one kind of the fused polycyclic aromatic compound according to claim 2.

7. A display apparatus comprising the organic light emitting device according to claim 6.

* * * * *